(12) United States Patent
McLuen et al.

(10) Patent No.: US 9,358,123 B2
(45) Date of Patent: Jun. 7, 2016

(54) BONE FUSION DEVICE, APPARATUS AND METHOD

(75) Inventors: Gary R. McLuen, Port Townsend, WA (US); Benjamin J. Remington, Modesto, CA (US); Daniel R. Baker, Seattle, WA (US); Joseph N. Logan, Trumbull, CT (US); Gregory C. Stalcup, Columbia City, IN (US); Daniel E. Gerbec, Logan, UT (US)

(73) Assignee: Neuropro Spinal Jaxx, Inc., Modesto, CA (US)

( * ) Notice: Subject to any disclaimer, the term of this patent is extended or adjusted under 35 U.S.C. 154(b) by 0 days.

(21) Appl. No.: 13/571,265

(22) Filed: Aug. 9, 2012

(65) Prior Publication Data
US 2013/0211525 A1    Aug. 15, 2013

Related U.S. Application Data

(60) Provisional application No. 61/521,682, filed on Aug. 9, 2011.

(51) Int. Cl.
*A61F 2/44* (2006.01)
*A61F 2/46* (2006.01)
*A61F 2/30* (2006.01)

(52) U.S. Cl.
CPC .............. *A61F 2/4455* (2013.01); *A61F 2/442* (2013.01); *A61F 2/447* (2013.01); *A61F 2/4611* (2013.01); *A61F 2/30767* (2013.01); *A61F 2/30965* (2013.01); *A61F 2002/3008* (2013.01); *A61F 2002/30013* (2013.01); *A61F 2002/3041* (2013.01); *A61F 2002/3052* (2013.01); *A61F 2002/3093* (2013.01); *A61F 2002/30265* (2013.01); *A61F 2002/30365* (2013.01);
(Continued)

(58) Field of Classification Search
CPC ................ A61F 2/4425; A61F 2/4611; A61F 2002/30576
USPC ............. 623/17.11–17.16; 606/99, 105, 86 B
See application file for complete search history.

(56) References Cited

U.S. PATENT DOCUMENTS 4,309,777 A    1/1982  Patil
4,599,086 A *  7/1986  Doty ........................... 606/86 A
(Continued)

FOREIGN PATENT DOCUMENTS

JP        2274243        11/1990
WO      WO9117723        11/1991
(Continued)

OTHER PUBLICATIONS

Search Report from European Application No. EP13797446.

*Primary Examiner* — Eduardo C Robert
*Assistant Examiner* — Michelle C Eckman
(74) *Attorney, Agent, or Firm* — Haverstock & Owens LLP

(57) ABSTRACT

A bone fusion method, apparatus and device for insertion between bones that are to be fused together and/or in place of one or more of the bones, such as, for example, the vertebrae of a spinal column. The bone fusion device comprises one or more extendable plates having a central rib. The bone fusion device includes one or more support channels configured to receive an insertion instrument that is then secured to the bone fusion device via a coupling mechanism. As a result, the coupled device is able to be securely positioned between vertebrae using the insertion instrument with minimal risk of slippage.

17 Claims, 14 Drawing Sheets

(52) U.S. Cl.
CPC .......... *A61F2002/30367* (2013.01); *A61F 2002/30372* (2013.01); *A61F 2002/30373* (2013.01); *A61F 2002/30395* (2013.01); *A61F 2002/30397* (2013.01); *A61F 2002/30403* (2013.01); *A61F 2002/30405* (2013.01); *A61F 2002/30411* (2013.01); *A61F 2002/30413* (2013.01); *A61F 2002/30415* (2013.01); *A61F 2002/30482* (2013.01); *A61F 2002/30484* (2013.01); *A61F 2002/30507* (2013.01); *A61F 2002/30509* (2013.01); *A61F 2002/30517* (2013.01); *A61F 2002/30522* (2013.01); *A61F 2002/30528* (2013.01); *A61F 2002/30579* (2013.01); *A61F 2002/30596* (2013.01); *A61F 2002/30598* (2013.01); *A61F 2002/30601* (2013.01); *A61F 2002/30616* (2013.01); *A61F 2002/30777* (2013.01); *A61F 2002/30784* (2013.01); *A61F 2002/30827* (2013.01); *A61F 2002/30841* (2013.01); *A61F 2002/30843* (2013.01); *A61F 2002/30904* (2013.01); *A61F 2002/4475* (2013.01); *A61F 2002/4622* (2013.01); *A61F 2002/4627* (2013.01); *A61F 2310/00023* (2013.01)

(56) References Cited

U.S. PATENT DOCUMENTS

| Patent No. | Kind | Date | Inventor | Ref |
|---|---|---|---|---|
| 4,636,217 A * | | 1/1987 | Ogilvie et al. | 623/17.11 |
| 4,767,040 A | | 8/1988 | Miller et al. | |
| 4,863,476 A | | 9/1989 | Shepperd | |
| 4,892,545 A * | | 1/1990 | Day et al. | 623/17.11 |
| 4,961,740 A | | 10/1990 | Ray et al. | |
| 5,015,247 A | | 5/1991 | Michelson | |
| 5,059,193 A | | 10/1991 | Kuslich | |
| 5,123,926 A | | 6/1992 | Pisharodi | |
| 5,171,278 A | | 12/1992 | Pisharodi | |
| 5,443,514 A | | 8/1995 | Steffee | |
| 5,458,642 A | | 10/1995 | Beer et al. | |
| 5,522,899 A | | 6/1996 | Michelson | |
| 5,653,763 A | | 8/1997 | Errico et al. | |
| 5,658,335 A | | 8/1997 | Allen | |
| 5,665,122 A | | 9/1997 | Kambin | |
| 5,693,100 A | | 12/1997 | Pisharodi | |
| 5,702,391 A * | | 12/1997 | Lin | 623/17.11 |
| 5,716,415 A | | 2/1998 | Steffee | |
| 5,782,832 A | | 7/1998 | Larsen et al. | |
| 5,800,547 A * | | 9/1998 | Schafer et al. | 623/17.16 |
| 5,800,550 A | | 9/1998 | Sertich | |
| 5,827,328 A | | 10/1998 | Buttermann | |
| 5,865,848 A | | 2/1999 | Baker | |
| 5,885,287 A | | 3/1999 | Bagby | |
| 5,928,284 A | | 7/1999 | Mehdizadeh | |
| 5,980,522 A | | 11/1999 | Koros et al. | |
| 6,045,579 A | | 4/2000 | Hochshuler et al. | |
| 6,080,158 A | | 6/2000 | Lin | |
| 6,080,193 A | | 6/2000 | Hochshuler et al. | |
| 6,102,949 A | | 8/2000 | Biedermann et al. | |
| 6,102,950 A | | 8/2000 | Vaccaro | |
| 6,117,174 A | | 9/2000 | Nolan | |
| 6,129,763 A | | 10/2000 | Chauvin et al. | |
| 6,156,067 A | | 12/2000 | Bryan et al. | |
| 6,159,244 A | | 12/2000 | Suddaby | |
| 6,174,334 B1 | | 1/2001 | Suddaby | |
| 6,176,881 B1 | | 1/2001 | Schar et al. | |
| 6,176,882 B1 * | | 1/2001 | Biedermann et al. | 623/17.15 |
| 6,179,873 B1 | | 1/2001 | Zientek | |
| 6,183,517 B1 | | 2/2001 | Suddaby | |
| 6,190,414 B1 * | | 2/2001 | Young et al. | 623/17.15 |
| 6,231,609 B1 | | 5/2001 | Mehdizadeh | |
| 6,325,827 B1 | | 12/2001 | Lin | |
| 6,342,074 B1 | | 1/2002 | Simpson | |
| 6,371,968 B1 | | 4/2002 | Kogasaka et al. | |
| 6,371,987 B1 | | 4/2002 | Weiland et al. | |
| 6,375,655 B1 | | 4/2002 | Zdeblick et al. | |
| 6,375,683 B1 | | 4/2002 | Crozet et al. | |
| 6,409,766 B1 | | 6/2002 | Brett | |
| 6,419,705 B1 | | 7/2002 | Erickson | |
| 6,436,140 B1 | | 8/2002 | Liu et al. | |
| 6,443,989 B1 | | 9/2002 | Jackson | |
| 6,454,806 B1 | | 9/2002 | Cohen et al. | |
| 6,454,807 B1 | | 9/2002 | Jackson | |
| 6,464,727 B1 | | 10/2002 | Sharkey et al. | |
| 6,488,710 B2 | | 12/2002 | Besselink | |
| 6,491,695 B1 | | 12/2002 | Roggenbuck | |
| 6,527,803 B1 * | | 3/2003 | Crozet et al. | 623/17.11 |
| 6,562,041 B1 | | 5/2003 | Yonemura et al. | |
| 6,572,619 B2 | | 6/2003 | Santilli | |
| 6,572,653 B2 | | 6/2003 | Simonson | |
| 6,576,016 B1 * | | 6/2003 | Hochshuler et al. | 623/17.15 |
| 6,582,431 B1 | | 6/2003 | Ray | |
| 6,582,467 B1 | | 6/2003 | Teitelbaum et al. | |
| 6,595,995 B2 | | 7/2003 | Zdeblick et al. | |
| 6,613,091 B1 | | 9/2003 | Zdeblick et al. | |
| 6,645,249 B2 | | 11/2003 | Ralph et al. | |
| 6,652,584 B2 | | 11/2003 | Michelson | |
| 6,666,888 B1 | | 12/2003 | Jackson | |
| 6,685,742 B1 | | 2/2004 | Jackson | |
| 6,706,070 B1 | | 3/2004 | Wagner et al. | |
| 6,709,458 B2 | | 3/2004 | Michelson | |
| 6,723,126 B1 | | 4/2004 | Berry | |
| 6,723,128 B2 | | 4/2004 | Uk | |
| 6,746,454 B2 | | 6/2004 | Winterbottom et al. | |
| 6,767,367 B1 * | | 7/2004 | Michelson | 623/17.16 |
| 6,770,095 B2 | | 8/2004 | Grinberg et al. | |
| 6,770,096 B2 * | | 8/2004 | Bolger et al. | 623/17.16 |
| 6,808,537 B2 | | 10/2004 | Michelson | |
| 6,821,298 B1 | | 11/2004 | Jackson | |
| 6,830,589 B2 | | 12/2004 | Erickson | |
| 6,835,206 B2 | | 12/2004 | Jackson | |
| 6,902,568 B2 | | 6/2005 | Serhan | |
| 6,923,830 B2 | | 8/2005 | Michelson | |
| 6,942,698 B1 | | 9/2005 | Jackson | |
| 6,962,606 B2 | | 11/2005 | Michelson | |
| 6,979,353 B2 | | 12/2005 | Bresina | |
| 6,989,011 B2 | | 1/2006 | Paul et al. | |
| 7,008,453 B1 | | 3/2006 | Michelson | |
| 7,018,415 B1 | | 3/2006 | McKay | |
| 7,041,309 B2 | | 5/2006 | Remington et al. | |
| 7,048,763 B2 | | 5/2006 | Ralph et al. | |
| 7,094,257 B2 | | 8/2006 | Mujwid et al. | |
| 7,108,862 B2 | | 9/2006 | Remington et al. | |
| 7,118,598 B2 | | 10/2006 | Michelson | |
| 7,128,760 B2 | | 10/2006 | Michelson | |
| 7,166,130 B2 | | 1/2007 | Ferree | |
| 7,195,643 B2 | | 3/2007 | Jackson | |
| 7,211,112 B2 | | 5/2007 | Baynham et al. | |
| 7,217,291 B2 | | 5/2007 | Zucherman et al. | |
| 7,217,293 B2 | | 5/2007 | Branch, Jr. | |
| 7,220,280 B2 | | 5/2007 | Kast et al. | |
| 7,220,282 B2 | | 5/2007 | Kuslich | |
| 7,235,103 B2 | | 6/2007 | Rivin | |
| 7,238,186 B2 | | 7/2007 | Zdeblick et al. | |
| 7,323,011 B2 | | 1/2008 | Shepard et al. | |
| 7,331,994 B2 | | 2/2008 | Gordon et al. | |
| 7,331,996 B2 | | 2/2008 | Soto et al. | |
| 7,431,735 B2 | | 10/2008 | Liu et al. | |
| 7,445,636 B2 | | 11/2008 | Michelson | |
| 7,479,160 B2 | | 1/2009 | Branch et al. | |
| 7,500,992 B2 | | 3/2009 | Li | |
| 7,537,612 B2 | | 5/2009 | Kunzler | |
| 7,578,849 B2 | | 8/2009 | Trieu | |
| 7,584,682 B2 | | 9/2009 | Hsiao | |
| 7,588,573 B2 * | | 9/2009 | Berry | 606/86 A |
| 7,594,932 B2 * | | 9/2009 | Aferzon et al. | 623/17.16 |
| 7,608,107 B2 | | 10/2009 | Michelson | |
| 7,621,956 B2 | | 11/2009 | Paul et al. | |
| 7,674,296 B2 | | 3/2010 | Rhonda et al. | |
| 7,678,148 B2 | | 3/2010 | Peterman | |
| 7,682,376 B2 | | 3/2010 | Trieu | |
| 7,691,147 B2 | | 4/2010 | Gutlin et al. | |
| 7,703,727 B2 | | 4/2010 | Selness | |
| 7,704,279 B2 * | | 4/2010 | Moskowitz et al. | 623/17.11 |

(56) References Cited

U.S. PATENT DOCUMENTS

| | | | |
|---|---|---|---|
| 7,708,778 B2* | 5/2010 | Gordon et al. | 623/17.15 |
| 7,727,280 B2* | 6/2010 | McLuen | 623/17.16 |
| 7,749,252 B2 | 7/2010 | Zucherman et al. | |
| 7,753,958 B2* | 7/2010 | Gordon et al. | 623/17.15 |
| 7,758,617 B2 | 7/2010 | Lott et al. | |
| 7,794,501 B2 | 9/2010 | Edie et al. | |
| 7,799,081 B2 | 9/2010 | McKinley | |
| D626,233 S | 10/2010 | Cipoletti et al. | |
| 7,811,287 B2 | 10/2010 | Errico et al. | |
| 7,811,327 B2 | 10/2010 | Hansell et al. | |
| 7,828,849 B2 | 11/2010 | Lim | |
| 7,837,688 B2 | 11/2010 | Boyer, II et al. | |
| 7,837,734 B2 | 11/2010 | Zucherman et al. | |
| 7,850,733 B2 | 12/2010 | Baynham et al. | |
| 7,931,688 B2 | 4/2011 | Landry et al. | |
| 7,932,825 B2 | 4/2011 | Berger | |
| RE42,480 E | 6/2011 | Bryan et al. | |
| 7,985,231 B2 | 7/2011 | Sankaran | |
| 8,002,834 B2 | 8/2011 | de Villiers et al. | |
| 8,062,374 B2* | 11/2011 | Markworth et al. | 623/17.16 |
| 8,062,375 B2* | 11/2011 | Glerum et al. | 623/17.16 |
| 8,070,813 B2 | 12/2011 | Grotz et al. | |
| 8,070,819 B2* | 12/2011 | Aferzon et al. | 623/17.16 |
| 8,075,593 B2* | 12/2011 | Hess | 606/248 |
| 8,105,382 B2* | 1/2012 | Olmos et al. | 623/17.15 |
| 8,110,004 B2 | 2/2012 | Valdevit et al. | |
| 8,114,131 B2* | 2/2012 | Kohm et al. | 606/248 |
| 8,118,870 B2* | 2/2012 | Gordon et al. | 623/17.16 |
| 8,118,871 B2* | 2/2012 | Gordon et al. | 623/17.16 |
| 8,123,810 B2* | 2/2012 | Gordon et al. | 623/17.16 |
| 8,142,479 B2* | 3/2012 | Hess | 606/248 |
| 8,147,550 B2* | 4/2012 | Gordon et al. | 623/17.15 |
| 8,167,950 B2* | 5/2012 | Aferzon et al. | 623/17.16 |
| 8,187,332 B2* | 5/2012 | McLuen | 623/17.16 |
| 8,221,502 B2 | 7/2012 | Branch, Jr. | |
| 8,262,666 B2 | 9/2012 | Baynham et al. | |
| 8,262,736 B2 | 9/2012 | Michelson | |
| 8,273,129 B2 | 9/2012 | Baynham et al. | |
| 8,282,683 B2 | 10/2012 | McLaughlin et al. | |
| 8,292,963 B2 | 10/2012 | Miller et al. | |
| 8,303,601 B2 | 11/2012 | Bandeira et al. | |
| 8,303,658 B2 | 11/2012 | Peterman | |
| 8,308,801 B2 | 11/2012 | Halverson et al. | |
| 8,308,804 B2 | 11/2012 | Krueger | |
| 8,317,025 B1 | 11/2012 | Kolozs et al. | |
| 8,328,962 B2 | 12/2012 | Schussler | |
| 8,337,562 B2 | 12/2012 | Landry et al. | |
| 8,343,222 B2 | 1/2013 | Cope | |
| 8,361,152 B2 | 1/2013 | McCormack et al. | |
| 8,366,777 B2* | 2/2013 | Matthis et al. | 623/17.16 |
| 8,366,779 B2* | 2/2013 | Dickson et al. | 623/17.16 |
| 8,377,140 B2* | 2/2013 | DeFalco et al. | 623/17.16 |
| 8,388,688 B2* | 3/2013 | Moore | 623/17.16 |
| 8,394,145 B2* | 3/2013 | Weiman | 623/17.16 |
| 8,403,990 B2 | 3/2013 | Dryer et al. | |
| 8,425,528 B2* | 4/2013 | Berry et al. | 606/99 |
| 8,444,696 B2 | 5/2013 | Michelson | |
| 8,444,697 B1 | 5/2013 | Butler et al. | |
| 8,535,380 B2* | 9/2013 | Greenhalgh et al. | 623/17.15 |
| 8,540,769 B2* | 9/2013 | Janowski et al. | 623/17.11 |
| 8,556,979 B2* | 10/2013 | Glerum et al. | 623/17.16 |
| 8,585,763 B2 | 11/2013 | Olevsky et al. | |
| 8,591,587 B2 | 11/2013 | Refai et al. | |
| 8,597,360 B2 | 12/2013 | McLuen et al. | |
| 8,690,886 B2 | 4/2014 | Fedorov et al. | |
| 8,740,980 B2 | 6/2014 | Merves | |
| 8,894,710 B2 | 11/2014 | Simpson et al. | |
| 2001/0016775 A1* | 8/2001 | Scarborough et al. | 623/17.16 |
| 2002/0029082 A1* | 3/2002 | Muhanna | 623/17.11 |
| 2002/0128716 A1* | 9/2002 | Cohen et al. | 623/17.15 |
| 2002/0165613 A1 | 11/2002 | Lin et al. | |
| 2003/0065396 A1* | 4/2003 | Michelson | 623/17.15 |
| 2003/0130739 A1* | 7/2003 | Gerbec et al. | 623/17.15 |
| 2004/0010312 A1* | 1/2004 | Enayati | 623/17.11 |
| 2004/0024461 A1 | 2/2004 | Ferree | |
| 2004/0039448 A1 | 2/2004 | Pisharodi | |
| 2004/0054412 A1* | 3/2004 | Gerbec et al. | 623/17.15 |
| 2004/0059271 A1* | 3/2004 | Berry | 602/32 |
| 2004/0087947 A1 | 5/2004 | Lim et al. | |
| 2004/0106998 A1 | 6/2004 | Ferree | |
| 2004/0127993 A1 | 7/2004 | Kast et al. | |
| 2004/0138750 A1 | 7/2004 | Mitchell | |
| 2004/0153156 A1* | 8/2004 | Cohen et al. | 623/17.13 |
| 2004/0181285 A1 | 9/2004 | Simonson | |
| 2004/0204762 A1 | 10/2004 | Ralph et al. | |
| 2004/0230309 A1 | 11/2004 | DiMauro et al. | |
| 2004/0243238 A1 | 12/2004 | Arnin et al. | |
| 2005/0015149 A1 | 1/2005 | Michelson | |
| 2005/0027362 A1* | 2/2005 | Williams et al. | 623/17.11 |
| 2005/0033429 A1* | 2/2005 | Kuo | 623/17.11 |
| 2005/0038515 A1 | 2/2005 | Kunzler | |
| 2005/0049590 A1* | 3/2005 | Alleyne et al. | 606/61 |
| 2005/0065610 A1 | 3/2005 | Pisharodi | |
| 2005/0107878 A1 | 5/2005 | Conchy | |
| 2005/0143825 A1* | 6/2005 | Enayati | 623/17.16 |
| 2005/0278036 A1 | 12/2005 | Leonard et al. | |
| 2005/0283236 A1 | 12/2005 | Razian | |
| 2006/0052872 A1 | 3/2006 | Studer et al. | |
| 2006/0069436 A1 | 3/2006 | Sutton et al. | |
| 2006/0095136 A1* | 5/2006 | McLuen | 623/23.47 |
| 2006/0116769 A1 | 6/2006 | Marnay et al. | |
| 2006/0122701 A1 | 6/2006 | Kiester | |
| 2006/0129244 A1 | 6/2006 | Ensign | |
| 2006/0142859 A1* | 6/2006 | McLuen | 623/17.11 |
| 2006/0149381 A1 | 7/2006 | Kim | |
| 2006/0190084 A1 | 8/2006 | Doubler et al. | |
| 2006/0200243 A1 | 9/2006 | Rothman et al. | |
| 2006/0241643 A1* | 10/2006 | Lim | A61B 17/025 606/90 |
| 2006/0241764 A1 | 10/2006 | Michelson | |
| 2006/0241766 A1 | 10/2006 | Felton et al. | |
| 2006/0241767 A1 | 10/2006 | Doty | |
| 2006/0241770 A1* | 10/2006 | Rhoda et al. | 623/17.15 |
| 2006/0241774 A1 | 10/2006 | Attali et al. | |
| 2006/0253201 A1* | 11/2006 | McLuen | 623/17.15 |
| 2006/0276899 A1 | 12/2006 | Zipnick et al. | |
| 2006/0293752 A1 | 12/2006 | Moumene et al. | |
| 2006/0293753 A1 | 12/2006 | Thramann | |
| 2007/0050030 A1 | 3/2007 | Kim | |
| 2007/0067038 A1 | 3/2007 | Studer et al. | |
| 2007/0093897 A1 | 4/2007 | Gerbee et al. | |
| 2007/0093901 A1 | 4/2007 | Grotz et al. | |
| 2007/0191954 A1* | 8/2007 | Hansell et al. | 623/17.15 |
| 2007/0233254 A1 | 10/2007 | Grotz et al. | |
| 2007/0255407 A1 | 11/2007 | Castleman et al. | |
| 2007/0255408 A1* | 11/2007 | Castleman et al. | 623/17.11 |
| 2007/0255410 A1* | 11/2007 | Dickson et al. | 623/17.11 |
| 2007/0255413 A1 | 11/2007 | Edie et al. | |
| 2007/0255415 A1 | 11/2007 | Edie et al. | |
| 2007/0270954 A1 | 11/2007 | Wu | |
| 2007/0270968 A1 | 11/2007 | Baynham et al. | |
| 2008/0009880 A1 | 1/2008 | Warnick et al. | |
| 2008/0015701 A1 | 1/2008 | Garcia et al. | |
| 2008/0021559 A1 | 1/2008 | Thramann | |
| 2008/0046083 A1 | 2/2008 | Hewko | |
| 2008/0051902 A1 | 2/2008 | Dwyer | |
| 2008/0077153 A1* | 3/2008 | Pernsteiner | A61F 2/4425 606/99 |
| 2008/0125778 A1 | 5/2008 | Li | |
| 2008/0132949 A1* | 6/2008 | Aferzon et al. | 606/246 |
| 2008/0140207 A1* | 6/2008 | Olmos et al. | 623/17.16 |
| 2008/0147193 A1* | 6/2008 | Matthis et al. | 623/17.16 |
| 2008/0154381 A1 | 6/2008 | Parrish | |
| 2008/0183293 A1 | 7/2008 | Parry et al. | |
| 2008/0208264 A1 | 8/2008 | Lazarof | |
| 2008/0243125 A1 | 10/2008 | Guzman et al. | |
| 2008/0243254 A1* | 10/2008 | Butler | 623/17.16 |
| 2008/0255666 A1* | 10/2008 | Fisher et al. | 623/17.16 |
| 2008/0269905 A1 | 10/2008 | Link | |
| 2008/0288076 A1 | 11/2008 | Soo et al. | |
| 2008/0306489 A1 | 12/2008 | Altarac et al. | |
| 2008/0306557 A1* | 12/2008 | Altarac et al. | 606/86 A |
| 2009/0048673 A1* | 2/2009 | Le Huec | 623/17.11 |
| 2009/0099601 A1* | 4/2009 | Aferzon et al. | 606/246 |

(56) References Cited

U.S. PATENT DOCUMENTS

| | | | |
|---|---|---|---|
| 2009/0112271 A1* | 4/2009 | Moskowitz et al. | 606/311 |
| 2009/0112325 A1* | 4/2009 | Refai et al. | 623/17.16 |
| 2009/0164020 A1* | 6/2009 | Janowski et al. | 623/17.16 |
| 2009/0192611 A1* | 7/2009 | Lindner | 623/17.11 |
| 2009/0198241 A1 | 8/2009 | Phan | |
| 2009/0198245 A1 | 8/2009 | Phan | |
| 2009/0198338 A1 | 8/2009 | Phan | |
| 2009/0210061 A1 | 8/2009 | Sledge | |
| 2009/0216330 A1* | 8/2009 | Geisert et al. | 623/17.16 |
| 2009/0222100 A1 | 9/2009 | Cipoletti et al. | |
| 2009/0222101 A1 | 9/2009 | de Villiers et al. | |
| 2009/0265007 A1* | 10/2009 | Colleran | 623/17.16 |
| 2009/0292361 A1 | 11/2009 | Lopez | |
| 2009/0299478 A1 | 12/2009 | Carls et al. | |
| 2010/0023057 A1 | 1/2010 | Aeschlimann et al. | |
| 2010/0042219 A1 | 2/2010 | Antonacci et al. | |
| 2010/0057204 A1 | 3/2010 | Kadaba et al. | |
| 2010/0100100 A1* | 4/2010 | Refai et al. | 606/99 |
| 2010/0100101 A1* | 4/2010 | Kraus | 606/99 |
| 2010/0145456 A1 | 6/2010 | Simpson et al. | |
| 2010/0204795 A1 | 8/2010 | Greenhalgh | |
| 2010/0211119 A1* | 8/2010 | Refai | A61F 2/44 606/86 A |
| 2010/0211176 A1* | 8/2010 | Greenhalgh | 623/17.15 |
| 2010/0222884 A1 | 9/2010 | Greenhalgh | |
| 2010/0234956 A1 | 9/2010 | Attia et al. | |
| 2010/0241231 A1 | 9/2010 | Marino et al. | |
| 2010/0256768 A1 | 10/2010 | Lim et al. | |
| 2010/0262247 A1 | 10/2010 | Arnin | |
| 2010/0280622 A1 | 11/2010 | McKinley | |
| 2010/0286779 A1 | 11/2010 | Thibodeau | |
| 2010/0286780 A1 | 11/2010 | Dryer et al. | |
| 2010/0292796 A1 | 11/2010 | Greenhalgh et al. | |
| 2010/0298939 A1 | 11/2010 | Delfosse et al. | |
| 2010/0305702 A1* | 12/2010 | Michelson | 623/17.11 |
| 2010/0324606 A1 | 12/2010 | Moskowitz et al. | |
| 2011/0015638 A1* | 1/2011 | Pischl et al. | 606/90 |
| 2011/0015747 A1 | 1/2011 | McManus et al. | |
| 2011/0035011 A1 | 2/2011 | Cain | |
| 2011/0054616 A1* | 3/2011 | Kamran et al. | 623/17.12 |
| 2011/0054621 A1 | 3/2011 | Lim | |
| 2011/0077738 A1 | 3/2011 | Ciupik et al. | |
| 2011/0087329 A1 | 4/2011 | Poulos | |
| 2011/0112587 A1* | 5/2011 | Patel et al. | 606/86 A |
| 2011/0130835 A1 | 6/2011 | Ashley et al. | |
| 2011/0130838 A1* | 6/2011 | Morgenstern Lopez | 623/17.16 |
| 2011/0138948 A1 | 6/2011 | Jimenez et al. | |
| 2011/0160861 A1 | 6/2011 | Jimenez et al. | |
| 2011/0172716 A1 | 7/2011 | Glerum | |
| 2011/0172774 A1 | 7/2011 | Varela | |
| 2011/0213465 A1 | 9/2011 | Landry et al. | |
| 2011/0218627 A1 | 9/2011 | Rampersaud et al. | |
| 2011/0230970 A1 | 9/2011 | Lynn et al. | |
| 2011/0238184 A1 | 9/2011 | Zdeblick et al. | |
| 2011/0282453 A1 | 11/2011 | Greenhalgh et al. | |
| 2011/0301712 A1 | 12/2011 | Palmatier et al. | |
| 2011/0319997 A1* | 12/2011 | Glerum | A61F 2/447 623/17.15 |
| 2012/0029644 A1* | 2/2012 | Markworth et al. | 623/17.16 |
| 2012/0035727 A1* | 2/2012 | Lins | 623/17.11 |
| 2012/0035729 A1* | 2/2012 | Glerum et al. | 623/17.15 |
| 2012/0046748 A1* | 2/2012 | Weiman | 623/17.16 |
| 2012/0046751 A1* | 2/2012 | Muhanna et al. | 623/17.16 |
| 2012/0058451 A1 | 3/2012 | Lazarof | |
| 2012/0059470 A1 | 3/2012 | Weiman | |
| 2012/0059471 A1* | 3/2012 | Keller | 623/17.11 |
| 2012/0059472 A1 | 3/2012 | Weiman | |
| 2012/0059473 A1 | 3/2012 | Weiman | |
| 2012/0059474 A1 | 3/2012 | Weiman | |
| 2012/0059475 A1 | 3/2012 | Weiman | |
| 2012/0059481 A1 | 3/2012 | Abernathie et al. | |
| 2012/0064487 A1 | 3/2012 | Lazarof | |
| 2012/0064488 A1 | 3/2012 | Lazarof | |
| 2012/0071979 A1 | 3/2012 | Zipnick | |
| 2012/0089228 A1 | 4/2012 | Poulos | |
| 2012/0130494 A1 | 5/2012 | DeLurio et al. | |
| 2012/0136448 A1 | 5/2012 | Seifert et al. | |
| 2012/0143194 A1 | 6/2012 | Seifert et al. | |
| 2012/0143201 A1 | 6/2012 | Seifert et al. | |
| 2012/0143340 A1* | 6/2012 | Aferzon et al. | 623/17.16 |
| 2012/0150241 A1* | 6/2012 | Ragab et al. | 606/86 A |
| 2012/0150304 A1 | 6/2012 | Glerum et al. | |
| 2012/0150305 A1 | 6/2012 | Glerum et al. | |
| 2012/0158071 A1* | 6/2012 | Jimenez et al. | 606/86 A |
| 2012/0158146 A1 | 6/2012 | Glerum et al. | |
| 2012/0158147 A1 | 6/2012 | Glerum et al. | |
| 2012/0158148 A1 | 6/2012 | Glerum et al. | |
| 2012/0179255 A1* | 7/2012 | DeFalco et al. | 623/17.11 |
| 2012/0191194 A1 | 7/2012 | Olmos et al. | |
| 2012/0197299 A1* | 8/2012 | Fabian, Jr. | 606/279 |
| 2012/0197317 A1* | 8/2012 | Lezama et al. | 606/86 A |
| 2012/0197404 A1 | 8/2012 | Brun et al. | |
| 2012/0203347 A1 | 8/2012 | Glerum et al. | |
| 2012/0209384 A1* | 8/2012 | Arnold et al. | 623/17.15 |
| 2012/0226357 A1 | 9/2012 | Varela | |
| 2012/0232601 A1 | 9/2012 | Chabansky et al. | |
| 2012/0245691 A1 | 9/2012 | Reimels | |
| 2012/0265259 A1* | 10/2012 | LaPosta et al. | 606/86 A |
| 2012/0271422 A1 | 10/2012 | Miller et al. | |
| 2012/0277865 A1* | 11/2012 | Trieu et al. | 623/17.16 |
| 2012/0277867 A1* | 11/2012 | Kana et al. | 623/17.16 |
| 2012/0277875 A1 | 11/2012 | Arnin | |
| 2012/0290090 A1 | 11/2012 | Glerum et al. | |
| 2012/0303124 A1* | 11/2012 | McLuen et al. | 623/17.16 |
| 2012/0310350 A1 | 12/2012 | Farris et al. | |
| 2012/0323328 A1 | 12/2012 | Weiman | |
| 2012/0330421 A1 | 12/2012 | Weiman | |
| 2012/0330422 A1 | 12/2012 | Weiman | |
| 2013/0006358 A1* | 1/2013 | Olevsky et al. | 623/17.16 |
| 2013/0006359 A1* | 1/2013 | Fedorov et al. | 623/17.16 |
| 2013/0006360 A1* | 1/2013 | Aferzon et al. | 623/17.16 |
| 2013/0006361 A1 | 1/2013 | Glerum et al. | |
| 2013/0006364 A1 | 1/2013 | McCormack et al. | |
| 2013/0018468 A1 | 1/2013 | Moskowitz et al. | |
| 2013/0018469 A1 | 1/2013 | Moskowitz et al. | |
| 2013/0018470 A1 | 1/2013 | Moskowitz et al. | |
| 2013/0023991 A1 | 1/2013 | Moskowitz et al. | |
| 2013/0023992 A1 | 1/2013 | Moskowitz et al. | |
| 2013/0023993 A1 | 1/2013 | Weiman | |
| 2013/0023994 A1 | 1/2013 | Glerum | |
| 2013/0030534 A1 | 1/2013 | DeLurio et al. | |
| 2013/0035724 A1 | 2/2013 | Fitzpatrick | |
| 2013/0035763 A1 | 2/2013 | Krueger | |
| 2013/0053962 A1 | 2/2013 | Moskowitz et al. | |
| 2013/0053966 A1* | 2/2013 | Jimenez et al. | 623/17.16 |
| 2013/0085572 A1 | 4/2013 | Glerum et al. | |
| 2013/0103153 A1 | 4/2013 | Blackwell et al. | |
| 2013/0103156 A1 | 4/2013 | Packer et al. | |
| 2013/0110248 A1 | 5/2013 | Zipnick | |
| 2013/0123922 A1* | 5/2013 | McCormack | 623/17.12 |
| 2013/0144388 A1* | 6/2013 | Emery et al. | 623/17.16 |
| 2013/0158663 A1 | 6/2013 | Miller et al. | |
| 2013/0158664 A1 | 6/2013 | Palmatier et al. | |
| 2013/0158668 A1 | 6/2013 | Nichols et al. | |
| 2013/0158669 A1 | 6/2013 | Sungarian et al. | |
| 2013/0190874 A1* | 7/2013 | Glazer | 623/17.11 |
| 2013/0197641 A1* | 8/2013 | Shepard et al. | 623/17.11 |
| 2013/0197642 A1* | 8/2013 | Ernst | 623/17.16 |
| 2013/0197647 A1* | 8/2013 | Wolters et al. | 623/17.16 |
| 2013/0204371 A1* | 8/2013 | McLuen et al. | 623/17.16 |
| 2013/0211525 A1* | 8/2013 | McLuen et al. | 623/17.16 |
| 2013/0231747 A1* | 9/2013 | Olmos et al. | 623/17.16 |
| 2013/0245767 A1* | 9/2013 | Lee et al. | 623/17.16 |
| 2013/0253650 A1 | 9/2013 | Ashley et al. | |
| 2013/0274883 A1* | 10/2013 | McLuen et al. | 623/17.16 |
| 2013/0282120 A1* | 10/2013 | Refai et al. | 623/17.11 |
| 2013/0310938 A1 | 11/2013 | Soumac et al. | |
| 2014/0088708 A1 | 3/2014 | McLaughlin et al. | |
| 2014/0156006 A1 | 6/2014 | Bannigan et al. | |
| 2014/0236296 A1 | 8/2014 | Wagner et al. | |
| 2014/0249629 A1 | 9/2014 | Moskowitz et al. | |
| 2014/0257485 A1 | 9/2014 | Matthis et al. | |
| 2014/0277470 A1 | 9/2014 | Baynham | |
| 2014/0277500 A1 | 9/2014 | Logan et al. | |

(56) References Cited

U.S. PATENT DOCUMENTS

| | | |
|---|---|---|
| 2014/0277509 A1 | 9/2014 | Robinson et al. |
| 2014/0288652 A1 | 9/2014 | Boehm et al. |
| 2014/0316522 A1 | 10/2014 | Weiman et al. |
| 2014/0343677 A1 | 11/2014 | Davis et al. |
| 2014/0343678 A1 | 11/2014 | Suddaby et al. |
| 2015/0094814 A1 | 4/2015 | Emerick et al. |

FOREIGN PATENT DOCUMENTS

| | | |
|---|---|---|
| WO | 2006134262 A1 | 12/2006 |
| WO | 2008035849 A1 | 3/2008 |
| WO | 2008086276 A2 | 7/2008 |
| WO | 2010045301 A1 | 4/2010 |
| WO | 2010121030 A2 | 10/2010 |
| WO | 2013023096 A1 | 2/2013 |

* cited by examiner

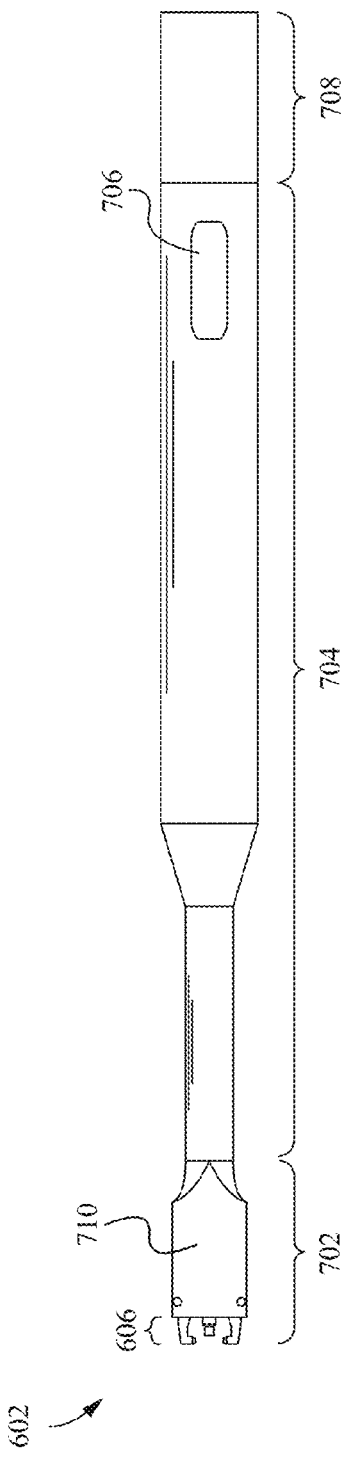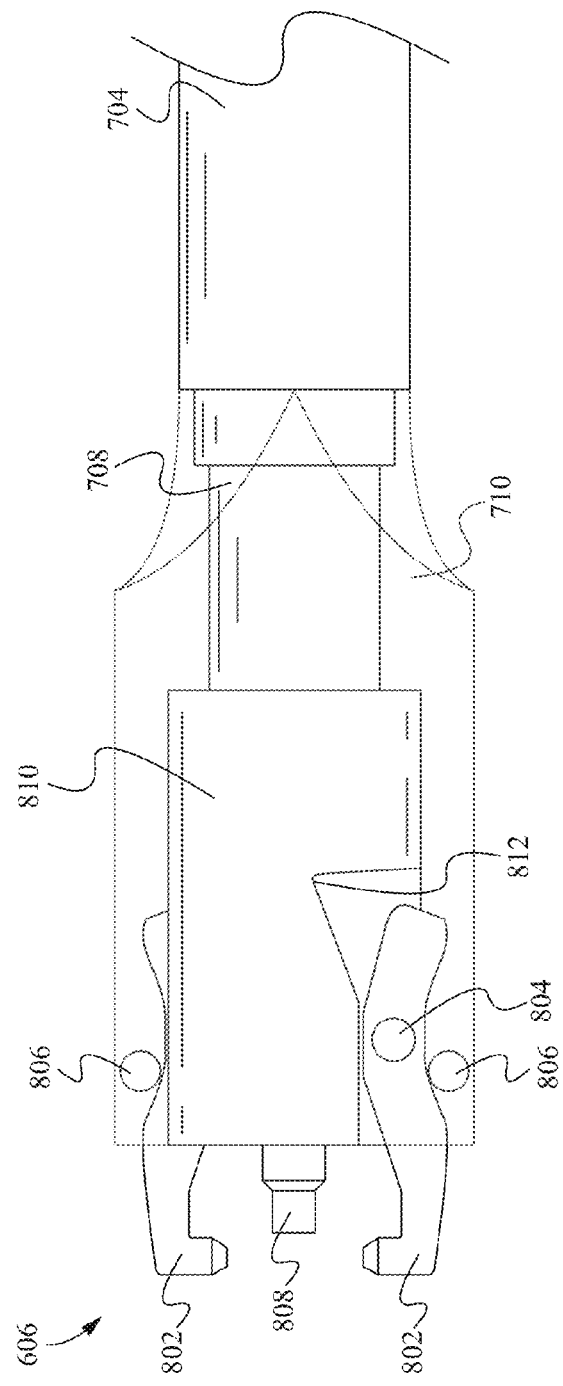

BONE FUSION DEVICE, APPARATUS AND METHOD

RELATED APPLICATIONS

This application claims priority under 35 U.S.C. §119(e) of U.S. Provisional Patent Application Ser. No. 61/521,682, filed Aug. 9, 2011, and entitled "BONE FUSION DEVICE, APPARATUS AND METHOD," which is hereby incorporated by reference.

FIELD OF THE INVENTION

This invention relates generally to bone fusion devices. More specifically, the present invention relates to devices for fusing vertebrae of the spine or other bones.

BACKGROUND OF THE INVENTION

The spinal column is made up of vertebrae stacked on top of one another. Between the vertebrae are discs which are gel-like cushions that act as shock-absorbers and keep the spine flexible. Injury, disease, or excessive pressure on the discs can cause degenerative disc disease or other disorders where the disc becomes thinner and allows the vertebrae to move closer together or become misaligned. Similarly, vertebrae are able to weaken due to impact or disease reducing their ability to properly distribute forces on the spine. As a result, nerves may become pinched, causing pain that radiates into other parts of the body, or instability of the vertebrae may ensue.

One method for correcting disc and/or vertebrae-related disorders is to insert a fusion cage as a replacement for and/or in between the vertebrae to act as a structural replacement for the deteriorated disc and/or vertebrae. The fusion cage is typically a hollow metal device usually made of titanium. Once inserted, the fusion cage maintains the proper separation between the vertebrae to prevent nerves from being pinched and provides structural stability to the spine. Also, the inside of the cage is filled with bone graft material which eventually fuses permanently with the adjacent vertebrae into a single unit. However, it is difficult to retain this bone graft material in the cage and in the proper positions to stimulate bone growth.

The use of fusion cages for fusion and stabilization of vertebrae in the spine is known in the prior art. U.S. Pat. No. 4,961,740 to Ray, et al. entitled, "V-Thread Fusion Cage and Method of Fusing a Bone Joint," discloses a fusion cage with a threaded outer surface, where the crown of the thread is sharp and cuts into the bone. Perforations are provided in valleys between adjacent turns of the thread. The cage can be screwed into a threaded bore provided in the bone structure at the surgical site and then packed with bone chips which promote fusion.

U.S. Pat. No. 5,015,247 to Michelson entitled, "Threaded Spinal Implant," discloses a fusion implant comprising a cylindrical member having a series of threads on the exterior of the cylindrical member for engaging the vertebrae to maintain the implant in place and a plurality of openings in the cylindrical surface.

U.S. Pat. No. 6,342,074 to Simpson entitled, "Anterior Lumbar Underbody Fusion Implant and Method For Fusing Adjacent Vertebrae," discloses a one-piece spinal fusion implant comprising a hollow body having an access passage for insertion of bone graft material into the intervertebral space after the implant has been affixed to adjacent vertebrae. The implant provides a pair of screw-receiving passages that are oppositely inclined relative to a central plane. In one embodiment, the screw-receiving passages enable the head of an orthopaedic screw to be retained entirely within the access passage.

U.S. Pat. No. 5,885,287 to Bagby entitled, "Self-tapping Interbody Bone Implant," discloses a bone joining implant with a rigid, implantable base body having an outer surface with at least one bone bed engaging portion configured for engaging between a pair of bone bodies to be joined, wherein at least one spline is provided by the bone bed engaging portion, the spline being constructed and arranged to extend outwardly of the body and having an undercut portion.

U.S. Pat. No. 6,582,467 to Teitelbaum et al. entitled,"Expandable Fusion Cage," discloses an expandable fusion cage where the surfaces of the cage have multiple portions cut out of the metal to form sharp barbs. As the cage is expanded, the sharp barbs protrude into the subcortical bone of the vertebrae to secure the cage in place. The cage is filled with bone or bone matrix material.

U.S. Pat. No. 5,800,550 to Sertich entitled, "Interbody Fusion Cage," discloses a prosthetic device which includes an inert generally rectangularly shaped support body adapted to be seated on hard end plates of vertebrae. The support body has top and bottom faces. A first peg is movably mounted in a first aperture located in the support body, and the first aperture terminates at one of the top and bottom faces of the support body. Further, the first peg projects away from the one of the top and bottom faces and into an adjacent vertebra to secure the support body in place relative to the vertebra.

U.S. Pat. No. 6,436,140 to Liu et al. entitled, "Expandable Interbody Fusion Cage and Method for Insertion," discloses an expandable hollow interbody fusion device, wherein the body is divided into a number of branches connected to one another at a fixed end and separated at an expandable end. The expandable cage may be inserted in its substantially cylindrical form and may be expanded by movement of an expansion member to establish lordosis of the spine. An expansion member interacts with the interior surfaces of the device to maintain the cage in the expanded condition and provide a large internal chamber for receiving bone in-growth material.

These patents all disclose fusion cage devices that can be inserted between vertebrae of the spine in an invasive surgical procedure. Such an invasive surgical procedure requires a long recovery period.

SUMMARY OF THE INVENTION

The present application is directed to a bone fusion method, apparatus and device for insertion between bones that are to be fused together and/or in place of one or more of the bones, such as, for example, the vertebrae of a spinal column. The bone fusion device comprises one or more extendable plates having a central rib. The bone fusion device is able to be inserted between or replace the vertebrae by using an minimally invasive procedure. The bone fusion device comprises one or more support channels configured to receive an insertion instrument that is then secured to the bone fusion device via a coupling mechanism. As a result, the coupled device is able to be securely positioned between vertebrae using the insertion instrument with minimal risk of slippage. After the device has been positioned between the vertebrae, and the screw is rotated by the control mechanism to deliver the bone graft material and extend the plates. Two plates are extended upon rotating a rotating means wherein extending blocks travel up the screw pushing out the angled plates as the extending blocks approach the ends of the bone fusion device. The central rib of the plates provides increased support against torsional forces creating more stable contact with the bones. In some embodiments, a single plate is extended. Thus, the plates are able to be advantageously positioned in the confined space between the vertebrae to help brace the device until the bone has fused.

One aspect of the present application is directed to a bone fusion system for inserting a bone fusion device into a desired location. The system comprises an insertion instrument comprising a coupling mechanism having a control mechanism and a plurality of fingers configured to move between a closed position wherein the fingers are close together to a spread position wherein the fingers are farther apart based on manipulation of the control mechanism and a bone fusion device having a body and one or more extendable tabs, wherein the body of the bone fusion device is detachably coupled to the insertion instrument by the coupling mechanism. In some embodiments, one or more of the fingers comprise a fingertip that protrudes laterally from the finger. In some embodiments, the body comprises one or more surface channels configured to receive the fingers and positioned along an exterior surface of the body. In some embodiments, the body comprises a front end and an interior cavity, and further wherein the channels are accessible from the front end and extend through the a plane perpendicular to the front end. In some embodiments, each of the surface channels comprise a gripping aperture for receiving the fingertip of the fingers of the gripping apparatus positioned within the surface channels. In some embodiments, the bone fusion device further comprises a positioning element having a positioning aperture and positioned through the front end and within the interior cavity of the body, and further wherein the positioning element is mechanically coupled with the extendable tabs such that moving the positioning element causes the extendable tabs to move with respect to the body. In some embodiments, the surface channels are positioned along the exterior surface on a plane perpendicular to the positioning aperture of the positioning element such that the fingers of the gripping apparatus are able to enter the one or more surface channels by moving parallel to the plane. In some embodiments, the insertion instrument further comprises a drive mechanism configured to engage with and selectively rotate the positioning aperture when the insertion instrument is coupled to the bone fusion device. In some embodiments, the control mechanism is coupled with the drive mechanism such that the drive mechanism is able to be rotated by manipulating the control mechanism. In some embodiments, the insertion instrument is configured to prevent rotation of the drive mechanism if the fingers are not in the closed position. In some embodiments, the insertion instrument comprises a locking mechanism that when activated by a trigger prevents rotation of the drive mechanism until the locking mechanism is deactivated by the trigger. In some embodiments, the insertion instrument comprises an indicator that indicates data corresponding to the amount of rotation of the drive mechanism. In some embodiments, the data indicated by the indicator indicates the current position of the tabs relative to the body of the bone fusion device. In some embodiments, the indicator is adjustable such that the indicator will indicate different data corresponding to the same amount of rotation of the drive mechanism based on the bone fusion device currently coupled to the insertion instrument.

Another aspect of the present application is directed to a method of operation of the bone fusion system. The method comprises spreading fingers of an insertion instrument with a control mechanism of the insertion instrument, sliding the fingers of the insertion instrument into one or more surface channels of a bone fusion device and inserting a drive mechanism of the insertion instrument into the positioning aperture of a positioning element of the bone fusion device, contracting the fingers with the control mechanism such that fingertips of the fingers move into gripping apertures of the surface channels and the insertion instrument is detachably coupled with the bone fusion device and positioning the bone fusion device into a desired position with the insertion instrument. In some embodiments, the method further comprises extending one or more extendable tabs of the bone fusion device by manipulating the control mechanism of the insertion instrument, wherein the control mechanism is mechanically coupled with the drive mechanism. In some embodiments, the method further comprises spreading the fingers with the control mechanism such that the fingertips of the fingers move out of the gripping apertures of the surface channels and sliding the fingers out of the surface channels of the bone fusion device and removing the drive mechanism from within the positioning aperture. In some embodiments, controlling the spreading the fingers comprises pulling or pushing the control mechanism in or out of a shaft of the insertion instrument. In some embodiments, extending the extendable tabs comprises rotating the control mechanism with respect to the fingers of the insertion instrument. In some embodiments, the method further comprises displaying data corresponding to the amount of rotation of the drive mechanism with an indicator on the insertion instrument. In some embodiments, the data indicated by the indicator indicates the current position of the tabs relative to the body of the bone fusion device. In some embodiments, the indicator is adjustable such that the indicator will indicate different data corresponding to the same amount of rotation of the drive mechanism based on the bone fusion device currently coupled to the insertion instrument. In some embodiments, the surface channels are configured to receive the fingers and positioned along an exterior surface of the body. In some embodiments, the body comprises a front end and an interior cavity, and further wherein the surface channels are accessible from the front end and extend through the a plane perpendicular to the front end. In some embodiments, the positioning element is positioned through the front end and within the interior cavity of the body, and further wherein the positioning element is mechanically coupled with the extendable tabs such that moving the positioning element causes the extendable tabs to move with respect to the body. In some embodiments, the surface channels are positioned along the exterior surface of the body on a plane perpendicular to the positioning aperture of the positioning element such that the fingers of the gripping apparatus are able to slide into the one or more surface channels by moving parallel to the plane. In some embodiments, the insertion instrument is configured to prevent rotation of the drive mechanism if the fingers are not fully contracted. In some embodiments, the insertion instrument comprises a locking mechanism that when activated by a trigger prevents rotation of the drive mechanism until the locking mechanism is deactivated by the trigger.

Another aspect of the present application is directed to an insertion instrument for inserting a bone fusion device into a desired location. The instrument comprises an elongated body and a coupling mechanism partially housed by the body and having a control mechanism and a plurality of fingers, wherein the plurality of fingers are configured to move between a closed position wherein the fingers are close together to a spread position, wherein the fingers are farther apart based on manipulation of the control mechanism. In some embodiments, one or more of the fingers comprise a fingertip that protrudes laterally from the finger. In some embodiments, the instrument further comprises a drive mechanism mechanically coupled with the control mechanism and configured to rotate with respect to the body. In some embodiments, the control mechanism enables selective rotation of the drive mechanism. In some embodiments, the instrument further comprises a stopping mechanism that is configured to prevent rotation of the drive mechanism if the fingers are not in the closed position. In some embodiments, the instrument further comprises a locking mechanism that when activated by a trigger prevents rotation of the drive mechanism until the locking mechanism is deactivated by the trigger. In some embodiments, the instrument further comprises an indicator that indicates data corresponding to the amount of rotation of the drive mechanism. In some embodiments, the data indicated by the indicator indicates the current position of extendable tabs of a bone fusion device coupled to the insertion instrument relative to a body of the bone fusion device. In some embodiments, the indicator is adjustable such that the indicator will indicate different data corresponding to the same amount of rotation of the drive mechanism based on the bone fusion device currently coupled to the insertion instrument.

BRIEF DESCRIPTION OF THE DRAWINGS

FIG. 7 illustrates a perspective view of the insertion instrument according to some embodiments.

FIG. 8A illustrates a detailed top view of the coupling mechanism within the cover according to some embodiments.

DETAILED DESCRIPTION

In the following description, numerous details and alternatives are set forth for purpose of explanation. However, one of ordinary skill in the art will realize that the invention can be practiced without the use of these specific details. For instance, the figures and description below often refer to the vertebral bones of a spinal column. However, one of ordinary skill in the art will recognize that some embodiments of the invention are practiced for the fusion of other bones, including broken bones and/or joints. In other instances, well-known structures and devices are shown in block diagram form in order not to obscure the description of the invention with unnecessary detail.

Figure 1A:
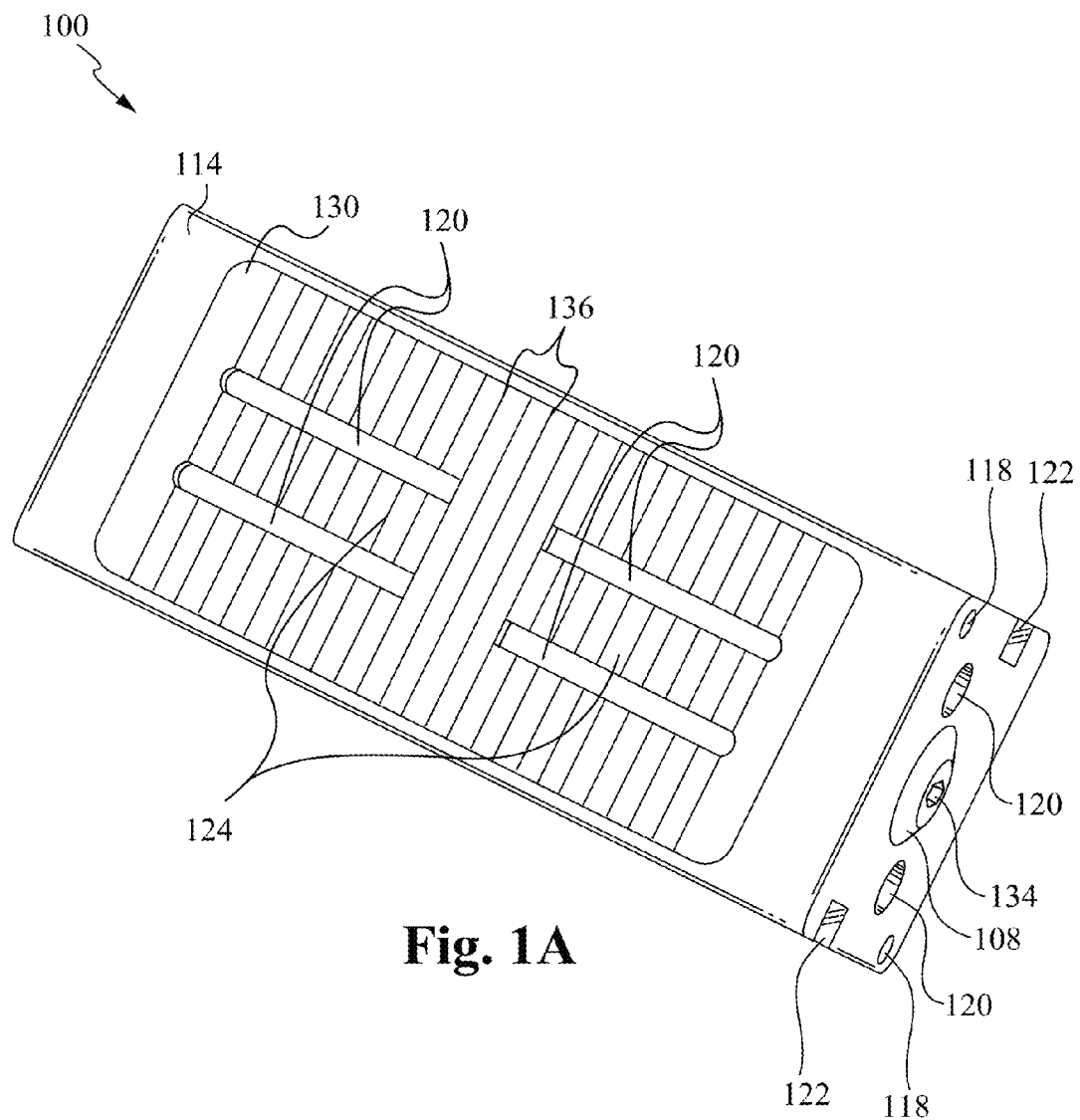
FIG. 1A illustrates a top perspective view of the bone fusion device according to some embodiments.
Figure 1B:
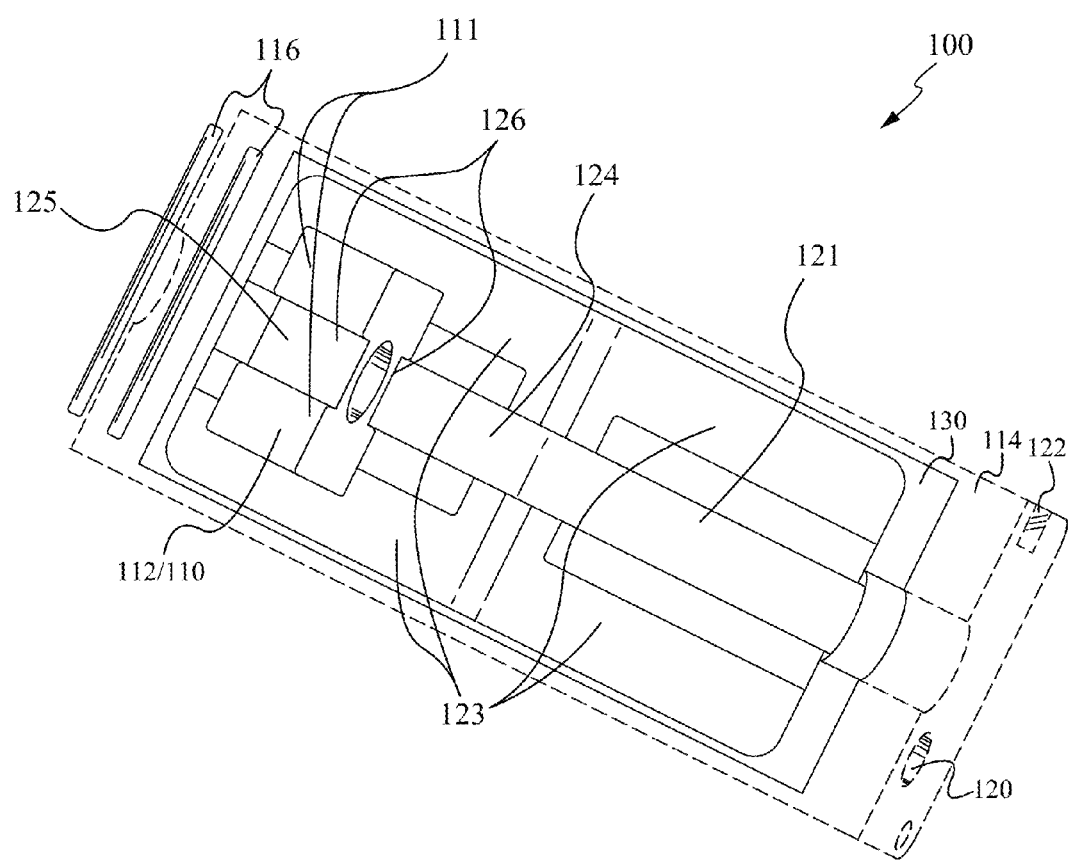
FIG. 1B illustrates a top cutout view of the bone fusion device according to some embodiments.

FIGS. 1A and 1B illustrate a top perspective and cutout view of the bone fusion device 100 according to some embodiments. As shown, the bone fusion device 100 has a substantially rectangular shape and has two end faces. The bone fusion device 100 is able to be constructed from a high strength biocompatible material, such as titanium, which has the strength to withstand compressive and shear forces in the spine that are generated by a patient's body weight and daily movements. Alternatively, part of all of the bone fusion device 100 is able to be constructed from one or more of the group consisting of high strength biocompatible material or a polymer such as PEEK, PEKK, and other polymeric materials know to be biocompatible and having sufficient strength. In some embodiments, the materials used to construct the bone fusion device include using additives, such as carbon fibers for better performance of the materials under various circumstances. The base biocompatible material is often textured or coated with a porous material conducive to the growth of new bone cells on the bone fusion device 100. The bone fusion device 100 has several conduits or holes 120 (also see FIG. 2) which permit the bone graft material to be inserted into the device 100 and to contact the vertebral bone before or after the device 100 has been inserted between the vertebrae of the patient. The bone graft material and the surface texturing of the device 100 encourage the growth and fusion of bone from the neighboring vertebrae. The fusion and healing process will result in the bone fusion device 100 aiding in the bridging of the bone between the two adjacent vertebral bodies of the spine which eventually fuse together during the healing period.

As further illustrated in FIGS. 1A and 1B, plates 130 are located on opposing sides of the bone fusion device 100. The plates 130 are shaped so that their outer surface is substantially flush with the frame 114 of the bone fusion device 100 in a nonextended position. Internally, the plates 130 have a central rib 124 and an angled inner surface. Specifically, the central rib 124 is configured to provide further outer surface area and structural support to the plates 130. Further, each plate 130 is shaped such that one or more angled surfaces 123 of the plate 130 for extending the plate 130 have end thicknesses that are larger than their middle thicknesses such that the thickness of the angled surfaces 123 gradually increases while going from the middle to the ends of the plate 130. A positioning means 108 within the frame 114 of the bone fusion device 100 comprises a positioning aperture 134, a first screw 102 and a second screw 104 coupled together (see FIGS. 4A and 4B). The positioning aperture 134 is configured to receive a drive/engaging mechanism 808 of a tool 602 (see FIGS. 6 and 8) such that the tool 602 is able to rotate the positioning means 108. The positioning aperture 134 is able to comprise numerous shapes and sizes as are well known in the art. The first screw 102 is threaded opposite of the second screw 104. For example, if the first screw 102 is left threaded, the second screw 104 is right threaded or vice versa. Furthermore, the first screw 102 is of a slightly different size than the second screw 104. The positioning means 108 is coupled to a first extending block 110 and a second extending block 112, each having a pair of rib slots 126 configured to receive the central ribs 124 of the plates 130 (see FIG. 1B). Specifically, the rib slots 126 are sized such that they permit the central ribs 124 to slide into and out of the slots 126 (depending on the position of the blocks 110, 112) such that when positioned within the slots 126, the blocks 110, 112 are able to support the plates 130 against torsional forces by holding and supporting the central ribs 124.

Further, the first extending block 110 is coupled to the first screw 102 and the second extending block 112 is coupled to the second screw 104, and the first extending block 110 and the second extending block 112 are positioned in the middle of the bone fusion device 100 in the compact position. When the positioning means 108 is turned appropriately, the extending blocks 110 and 112 each travel outwardly on their respective screws 102 and 104. As the extending blocks 110 and 112 travel outwardly, they push the plates 130 outward and the central ribs 124 slide within the rib slots 126. In other words, the inner plate surface 123 when in contact with the extending blocks 110, 112 act in such a manner so as to push the respective plates 130 apart. Specifically, the angled surfaces 111 of each extending block 110, 112 are able to be in contact with the plate surfaces 123 and the center rib surface 121 is in contact with the extending block slot surface 125. Thus, the plates 130 will be fully extended when the extending blocks 110 and 112 reach the opposite ends of the screws 102, 104. To retract the plates 130, the positioning device 108 is turned in the opposite direction and the extending blocks 110 and 112 will each travel back to the middle on their respective screws 102 and 104 with the central ribs 124 within the rib slots 126. When the extending blocks 110 and 112 are positioned in the middle of the bone fusion device 100, the plates 130 are compact and are within the frame 114 of the bone fusion device 100. It is contemplated that the operation of the device 100 is able to be reversed such that the plates 130, extending blocks 110, 112, and positioning means 108 are configured such that the extending blocks 110, 112 travel inwardly to extend the plates 130 into the extended position and travel outwardly to retract the plates 130 into the compact position. In any case, the nonextended plates 130 of the bone fusion device 100 provide a compact assembly that is suitable for insertion into the patient's body through a open, or minimally invasive surgical procedure. As used herein, an open or a minimally invasive procedure comprises a procedure wherein a smaller surgical incision is employed as compared to the size of the incision required for conventional invasive surgery, for example arthroscopic procedures. Moreover, minimally invasive procedures minimize or eliminate the need for excessive retraction of a patient's tissues such as muscles and nerves, thereby minimizing trauma and injury to the muscles and nerves and further reducing the patient's recovery time.

Figure 3:
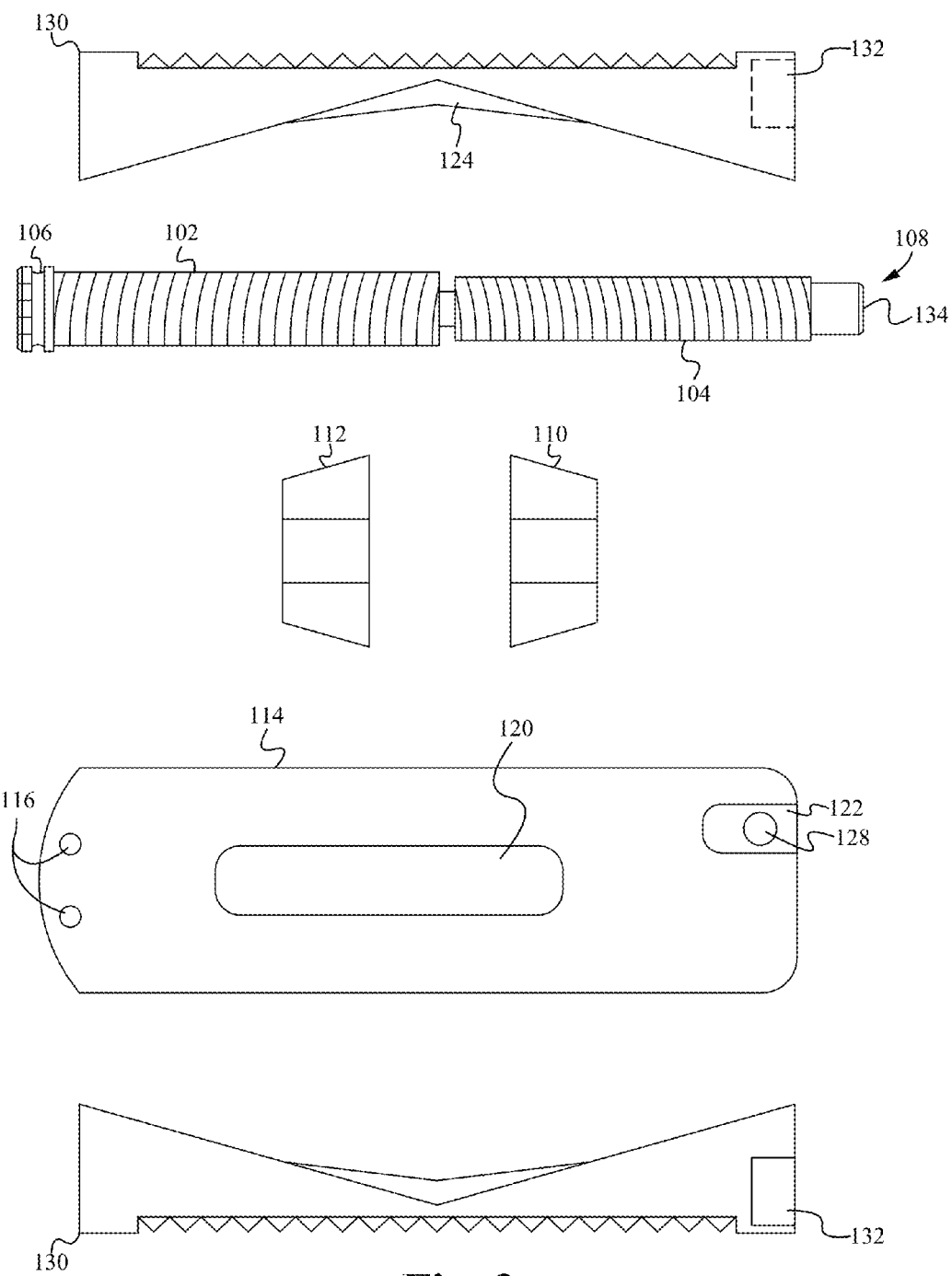
FIG. 3 illustrates a cross-sectional view of components of the bone fusion device according to some embodiments.

As the positioning means 108 is rotated causing the extending blocks 110 and 112 to move closer to the ends of the respective screws 102 and 104, the extending blocks 110 and 112 push the plates 130 outward causing the plates 130 to assert pressure against surrounding bones and securing the bone fusion device 100 in place. When the extending blocks 110 and 112 reach as close to the end of the positioning means 108 as allowed, the plates 130 are fully extended. Furthermore, since the extending blocks 110 and 112 travel along the positioning means 108, along the threads of the screws 102 and 104, very precise positions of the plates 130 are able to be achieved. The plates 130 are able to have serrated edges or teeth 136 to further increase the bone fusion device's gripping ability and therefore ability to be secured in place between the bones for both a long-term purchase and a short-term purchase. In some embodiments, the serrated edges or teeth 136 are able to be in a triangular or form a triangular wave formation as shown in FIG. 3. Alternatively, the serrated edges or teeth 136 are able to be filleted, chamfered, or comprise other teeth shapes or edge waves as are well known in the art.

To secure the bone fusion device 100 in place, a user generally utilizes an insertion instrument such as a screw driver to turn the positioning means 108. Screw drivers unfortunately have the ability to slip out of place. When performing surgery near someone's spine, it is preferable to prevent or at least minimize the slipping ability. Further, it is necessary to ensure that the surgeon is able to precisely place and control the device via a robust connection to the device. To do so, channels 122 having gripping apertures 128 are implemented to receive gripping fingers 802 (see FIG. 8) coupled to a tool/insertion instrument 602 (See FIG. 6) such that the tool 602 cannot slip out of place during operation. Specifically, the channels 122 are sized to receive the fingers 802 to prevent the tool 602 from moving laterally with respect to the head of the positioning means 108 and the gripping apertures 128 are sized to receive the fingertips 904 (see FIG. 9) of the tool 602 such that the fingers 802 (and tool 602) are unable to unintentionally be pulled out of the channels 122 (and positioning means 108). In some embodiments, the channels 122 are offset such that when facing the positioning aperture 134, one channel 122 is proximate the top left of the device 100 and the other channel 122 is proximate the bottom right of the device 100. Alternatively, the channels 122 are able to positioned on other portions of the frame 114. In operation, as described below in relation to FIGS. 6-10, a surgeon causes the fingers 802 of the tool 602 to spread as they are inserted into the channels 122 and then the surgeon causes the fingers 802 to clamp together inserting the fingertips 904 into the gripping apertures 128 and fully securing the tool 602 onto the device 100. Thus, the tool 602 is unable to slip out of place and is only able to be removed upon the spreading of the fingers 802 such that the fingertips 904 are removed from the apertures 128 and the fingers 802 are removed from the channels 122. Furthermore, if the device 100 is next to relatively immovable tissue (e.g. bone, ligament or tendon under load), then this device 100 will still be able to disengage, whereas one that relies on clamping by bending two rods together will not work if one of the rods is restricted by the relatively immovable tissue.

Figure 2:
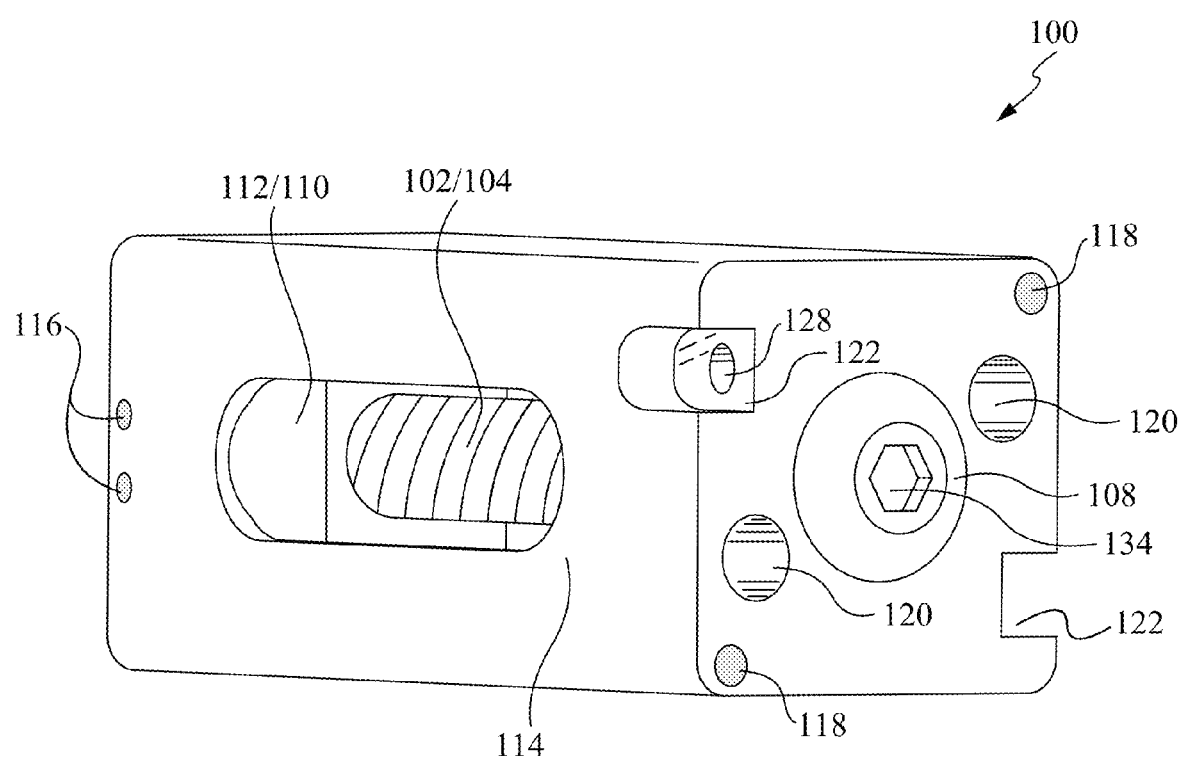
FIG. 2 illustrates a side perspective view of the bone fusion device according to some embodiments.

FIG. 2 illustrates a side perspective view of the bone fusion device 100 according to some embodiments. The bone fusion device 100 utilizes the positioning means 108 comprising the first screw 102 and the second screw 104 to move the first extending block 110 and the second extending block 112 outwardly from the middle of the bone fusion device 100 towards its ends. The positioning means 108 is held in place but permitted to turn utilizing one or more first pins 116. The one or more first pins 116 are secured within a retaining groove 106 (FIG. 3) of the positioning means 108. The extending blocks 110 and 112 force the plates 130 to either extend or retract depending on where the extending blocks 110 and 112 are positioned. As described above, the plates 130 are able to have serrated edges or teeth 136 to further increase gripping ability. The plates 130 are each coupled to the frame 114 of the bone fusion device 100 by one or more pin slots 132 (FIGS. 3 and 4A) and one or more second pins 118 wherein the one or more second pins 118 fit within the one or more pin slots 132 and are able to travel along the interior of the one or more pin slots 132. In some embodiments, each plate 130 is secured with a single second pin 118 and pin slot 132. Alternatively, one or more of the plates 130 are able to have multiple second pins 118 and pin slots 132. In some embodiments, the multiple pin slots 132 are able to be positioned at the corners of the plates 130 similar to the single pin slot 132 shown in FIG. 3. In some embodiments, the multiple pin slots 132 of plates 130 are symmetric such that any plate 130 is able to be placed on the top or bottom of the bone fusion device 100. Alternatively, the pin slots 132 of the plates 130 are able to be positioned anywhere on the plate 130 and/or be positioned asymmetrically. The holes/conduits 120 within the plates 130 allow the bone graft material to contact the vertebral bone after the device 100 has been inserted between the vertebrae of the patient. A set of holes/conduits 120 within the frame 114 also allow bone graft material to be inserted within the bone fusion device 100 after the bone fusion device 100 has been placed. The channels 122 having gripping apertures 128 implemented to receive a tool are shown as well. Alternatively, the gripping apertures 128 are able to be omitted.

FIG. 3 illustrates a cross-sectional view of components of the bone fusion device 100 according to some embodiments. As described above, the positioning means 108 comprises a first screw 102 and a second screw 104 wherein the first screw 102 is threaded differently than that of the second screw 104. Furthermore, the first screw 102 is of a slightly different size than the second screw 104. For example, in some embodiments the first screw 102 is an 8-32 screw and the second screw is a 6-32 screw. A retaining groove 106 is utilized to secure the positioning means 108 in place. In some embodiments, the retaining groove 106 is positioned opposite the end of the positioning means 108 having the positioning aperture 134. To ensure that the tool does not slip while turning the positioning means 108, the channels 122 having fingertip gripping apertures 128 are utilized to secure the tool as described above. Alternatively, the fingertip gripping apertures 128 are able to be omitted and the channels 122 are able to secure the tool as described above. A first extending block 110 and a second extending block 112 are utilized with the positioning means 108 to extend and compact one or more of plates 130. The first extending block 110 has an internal opening and threading to fit around the first screw 102. The second extending block 112 has an internal opening and threading to fit around the second screw 104. The frame 114 of the bone fusion device 100 contains a set of holes/conduits 120 within the frame 114 for allowing bone graft material to be inserted. Furthermore, one or more first pins 116 secure the positioning means within the frame 114. One or more second pins 116 in conjunction with one or more pin slots 132 secure the plates 130 to the frame 114.

Figure 4A:
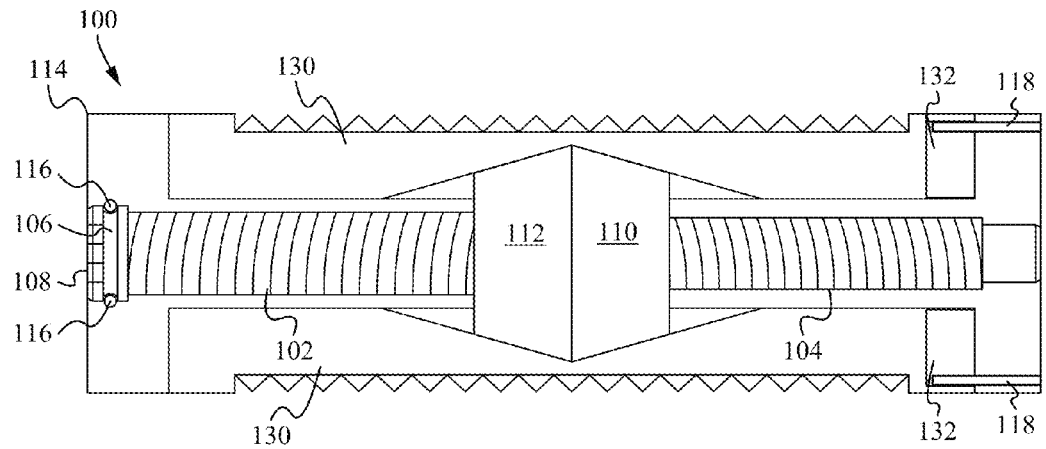
FIG. 4A illustrates a cross sectional view of the bone fusion device with the plates compacted according to some embodiments.

FIG. 4A illustrates a cross sectional view of the bone fusion device 100 with the plates retracted according to some embodiments. When the extending blocks 110 and 112 are positioned in the middle of the positioning means 108 with the first screw 102 and the second screw 104, the plates 130 are positioned within the frame 114 of the bone fusion device 100 with the central ribs 124 slid within the rib slots 126. The retaining groove 106 holds the positioning means 108 in place with one or more first pins 116. The plates 130 are coupled to the frame 114 of the bone fusion device 100 using the one or more slots 132 and the one or more second pins 118 wherein the one or more second pins 118 fit within the one or more slots 132 and are able to travel/slide along the interior of the one or more slots 132.

Figure 4B:
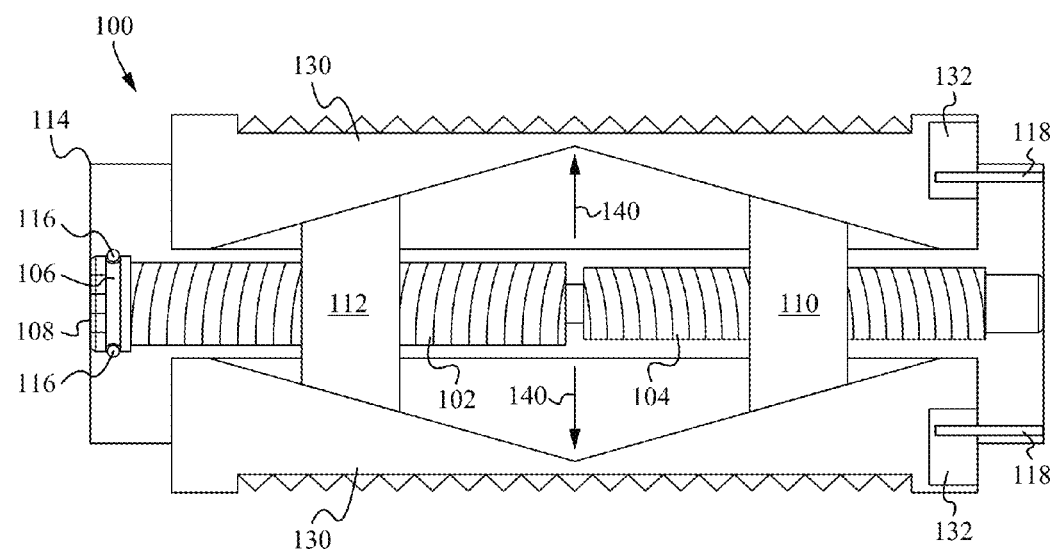
FIG. 4B illustrates a cross sectional view of the bone fusion device with the plates extended according to some embodiments.

FIG. 4B illustrates a cross sectional view of the bone fusion device 100 with the plates extended according to some embodiments. As shown in FIG. 4A, the bone fusion device 100 is compressed/contracted when the extending blocks 110 and 112 are in the middle of the bone fusion device 100. As a user turns the positioning means 108 via the positioning aperture 134, the extending blocks 110 and 112 gradually move outward from the middle. If the user turns the positioning means 108 in the opposite direction, the extending blocks move back towards the middle. As the extending blocks 110 and 112 are moving outward, the central ribs 124 slide out of the rib slots 126 and the extending blocks 110, 112 push on the plates 130. The plates 130 extend because the extending blocks 110 and 112 exert force against the angled plates 130 outwardly as shown by the arrows 140. When the extending blocks 110 and 112 are positioned near the ends of the bone fusion device 100, the plates 130 extend beyond the frame 114 of the bone fusion device 100 and ultimately secure the bone fusion device 100 between two bones. With the plates 130 coupled to the frame 114 of the bone fusion device 100 by the one or more slots 132 and the one or more second pins 118, the plates 130 are able to extend beyond the frame 114 of the bone fusion device 100 as the one or more second pins 118 travel within the interior of the one or more slots 132.

In operation, the bone fusion device 100 is initially configured in a compact position such that the extending blocks 110, 112 are located in the middle of the bone fusion device 100 thereby allowing the plates 130 to rest within the frame 114 of the bone fusion device 100. The compact bone fusion device 100 is then inserted into position within the patient. The surgeon is able to then the expand the bone fusion device 100 by rotating the positioning means 108 which moves the extending blocks 110, 112 towards the opposing ends of the bone fusion device 100—one near the head of the positioning means 108 and the other towards the tail of the positioning means. As the extending blocks 110, 112 move away from the middle, the plates 130 are pushed outwardly from the pressure of the extending blocks 110, 112 against the angled plates 130. Initially, the central ribs 124 of the plates 130 remain at least partially within the rib slots 126 of the extending blocks 110, 112 such that the blocks 110, 112 are able to resist torsional forces on the plates 130 and/or device 100. Gradually, the central ribs 124 slide out of the rib slots 126 as the extending blocks 110, 112 approach the ends of the positioning means 108. Alternatively, the central ribs 124 are able to be configured such that they remain at least partially within the rib slots 126 as the extending blocks 110, 112 approach the ends of the positioning means 108. Alternatively, the cental ribs 124 and/or rib slots 126 are able to be configured such that the central ribs 124 are fully within the rib slots 126, fully removed from the rib slots 126, or somewhere in between at any point along the path of the extending blocks 110, 112 from the center of the device to the ends of the device. Eventually the extending blocks 110, 112 exert a satisfactory force between the extended plates 130 and the bones to be fused. At that point the bone fusion device 100 is able to remain in place. Thereafter, material for fusing the bones together is inserted through the holes and openings 120 within the bone fusion device 100. Alternatively, the insertion of the material for fusing the bones together is able to be omitted.

Figure 5:
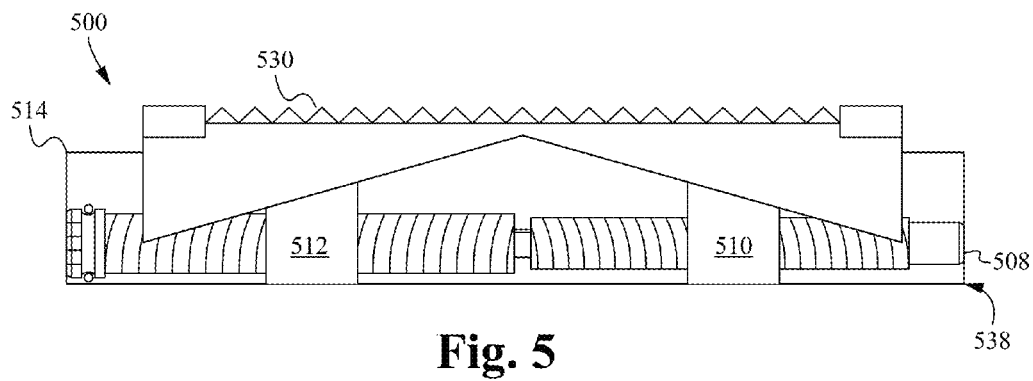
FIG. 5 illustrates a profile view of a bone fusion device having a single plate extension/retraction mechanism according to some embodiments.

FIG. 5 illustrates a bone fusion device 500 having a single plate extension/retraction mechanism according to some embodiments. The bone fusion device 500 shown in FIG. 5 is substantially similar to the bone fusion device 100 except for the differences described herein. In particular, the bone fusion device 500 comprises a half frame 514, one or more half extending blocks 510, 512, a plate 530 and positioning means 508. Similar to the bone fusion device 100, the half extending blocks 510, 512 are coupled around the positioning means 508 such that when the positioning means 508 are turned, the blocks 510, 512 move outwards causing the plate 530 to move to the extended position. The half frame 514 comprises a plate aperture (see FIG. 1A) for receiving the plate 530 and a solid floor 538 opposite the plate aperture. In some embodiments, the floor 538 is able to have one or more floor holes/conduits for receiving or distributing grafting material into and out of the device 500. In some embodiments, the device 500 is sized such that when the plate 530 is in the compact/retracted position the distance between the top of the plate 530 and the floor 538 is less than or equal to 5 mm, and when the plate 530 is in the extended position the distance between the top of the plate 530 and the floor 538 is less than or equal to 7 mm. Alternatively, the device 500 is sized such that when the plate 530 is in the compact/retracted position the distance between the top of the plate 530 and the floor 538 is in the range of 5 mm to 13 mm and when the plate 530 is in the extended position the distance between the top of the plate 530 and the floor 538 is in the range of 7 mm to 22 mm. Alternatively, other sizes of the device 500 are contemplated as are well known in the art. Thus, by including only a single plate 530, the height of the device 500 is able to be minimized. As a result, the bone fusion device 500 enables surgeons to use smaller incisions as well as to fit the bone fusion device 500 into smaller places and increasing the versatility of the device 500. Additionally, it should be noted that the single plate extension/retraction mechanism described in FIG. 5 is able to replace each of the dual or multiple plate extension/retraction mechanisms described herein wherein the devices having dual plate extension/retraction mechanisms are essentially halved (except for the positioning means) such that only one plate is remaining.

Figure 6:
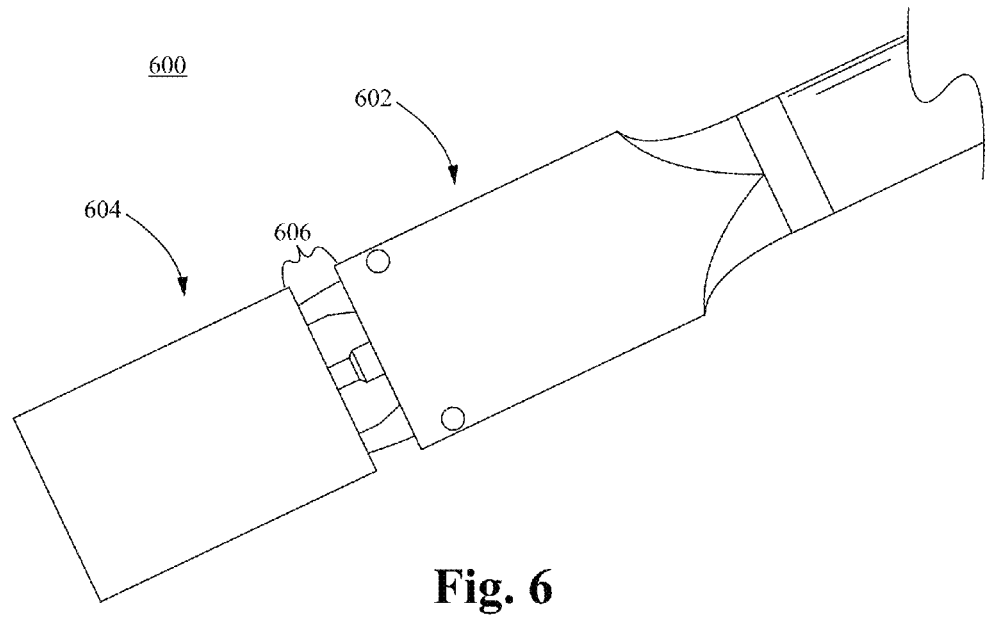
FIG. 6 illustrates a perspective view of a bone fusion apparatus according to some embodiments.

FIG. 6 illustrates a bone fusion apparatus 600 according to some embodiments. As shown in FIG. 6, the bone fusion apparatus 600 comprises a bone fusion insertion instrument 602 detachably coupled to a bone fusion device 604 via a coupling mechanism 606. In some embodiments, the bone fusion device 604 is substantially similar to the bone fusion device 100 described in FIGS. 1-5. Alternatively, the bone fusion device 604 is able to be other embodiments of bone fusion devices described herein or other types of bone fusion devices as are well known in the art. In some embodiments, the other types of bone fusion devices are able to be formed by one or more of polymers, bone, synthetic bone, metal or other biocompatible materials as are well known in the art. In some embodiments, the coupling mechanism 606 comprises a clamping mechanism. Alternatively, the coupling mechanism 606 is able to comprise any combination of a clamps, screws, locks, adhesives or other attachment elements as are well known in the art. In some embodiments, the insertion instrument 602 is able to detachably couple to a plurality of bone fusion devices 604 simultaneously such that the plurality of devices 604 are able to be simultaneously controlled (e.g. extension/contraction of the plates) by the single insertion instrument 602.

FIG. 7 illustrates a perspective view of the insertion instrument 602 according to some embodiments. As shown in FIG. 7, the insertion instrument 602 comprises a head 702 including the coupling mechanism 606 and a cover 710, a shaft 704 having a readout element 706, and a control mechanism 708 coupled to the coupling mechanism 606 through the shaft 704. The head 702 is sized such that the cross-section of the head is smaller than the cross section of the bone fusion device 604. The cover 710 is selectively retractable in order to enable easier/more thorough cleaning of the coupling mechanism 606 after use. Specifically, the cover 710 is able to be extended such that the cover 710 surrounds at least a portion of the coupling mechanism 606 in order to protect the coupling mechanism 606 (see FIG. 8) during operation, as well as being retracted exposing the previously covered portion of the coupling mechanism 606 for cleaning. The shaft 704 comprises a hollow tube that sheaths at least a portion of the control mechanism 708 and the connection of the control mechanism 708 to the coupling mechanism 606.

The readout element 706 is coupled to the control mechanism 708 and/or coupling mechanism 606 such that the readout element 706 is able to track the rotation of the drive mechanism 808 (see FIG. 8) of the coupling mechanism 606 in order to determine the current amount of extension of the plates 130. In some embodiments, the readout element 706 comprises a mechanical scale that mechanically tracks the rotations of the drive mechanism 808 and/or control mechanism 708. Alternatively, the readout element 706 is able to comprise an electronic or other type of scale capable of tracking the rotation of the drive mechanism 808 and/or control mechanism 708. In some embodiments, the readout element 706 comprises a replaceable and/or adjustable scale or other measurement/display device such that the scale is able to be adjusted and/or replaced by another scale based on the bone fusion device 604 to be coupled to the insertion instrument 602. For example, the scale is able to be selected/adjusted based on the amount each turn of the positioning element 108 of the bone fusion device 604 extends one or more of the plates 130. Thus, the readout element 706 provides the benefit of providing accurate readings of the extension amount of various types of bone fusion devices 604 to the users.

The control mechanism 708 is configured to enable a user to remotely attach/detach the coupling mechanism 606 to the bone fusion device 604 as well as remotely rotate the positioning means 108 of the device 604 by controlling the rotation of the drive mechanism 808. In some embodiments, the control mechanism 708 mechanically controls the coupling mechanism 606. For example, a user is able to release the coupling mechanism 606 from the bone fusion device 604 by pushing the control mechanism 708 into the shaft 704 and is able to couple the coupling mechanism 606 to the bone fusion device 604 by pulling out the control mechanism 708 from the shaft 704. Further, as another example, a user is able to rotate the drive mechanism 808 by rotating the control mechanism 708. Alternatively, the control mechanism 708 is able to control the coupling mechanism 606 by any combination of mechanically, pneumatically, electronically and other manners of controlling as are well known in the art. As a result, the control mechanism 708 provides the benefit of enabling a user to remotely control the coupling to the device 604, extension/retraction of the plates, and/or releasing of the device 604.

FIG. 8A illustrates a detailed top view of the coupling mechanism 606 within the cover 710 according to some embodiments. In some embodiments, the top view of the coupling mechanism 606 is substantially similar to the bottom view such that the coupling mechanism 606 is substantially symmetric. As shown in FIG. 8A, the coupling mechanism 606 comprises one or more fingers 802, one or more finger pins 804, one or more sliding pins 806, a drive mechanism 808 and a body 810. The drive mechanism 808 is coupled through the body 810 to the control mechanism 708. Specifically, the body 810 holds the drive mechanism 808 in place relative to the fingers 802, but enables the drive mechanism 808 to rotate in order to drive the bone fusion device 604 when desired. The fingers 802 are coupled to the body 810 with one or more finger pins 804 such that the fingers 802 are able to rotate about the one or more finger pins 804. In some embodiments, there is one finger pin 804 for each finger 802. The body 810 comprises one or more walls 812 that limit the rotation of the fingers 802 (based on the dimensions of the fingers 802) about the finger pins 804 to a preselected range of angles wherein at the greatest angle the fingers 802 are in an expanded/spread position and at the smallest angle the fingers 802 are in a closed position. In the spread position, the fingertips 904 (see FIG. 9) of the fingers 802 are separated by a distance greater than the distance between the surface of the gripping apertures 128 and/or the channels 122 having the gripping apertures 128. In the closed position, the fingertips 904 are separated by a distance equal to or less than the distance between the surface of the gripping apertures 128 and/or the channels 122 having the gripping apertures 128. Thus, when in the closed position, the fingertips 904 are able to enter the gripping apertures 128 and secure the coupling mechanism 606 to the bone fusion device 604, and when in the spread position, the fingertips 904 are able to be removed from the gripping apertures 128 thereby releasing the coupling mechanism 606 from the device 604. Alternatively, the fingertips 904 are able to be omitted and the separations in the spread and closed positions are determined by the distance between the fingers 802 (without fingertips 904).

The sliding pins 806 are coupled to the cover 710 and cause the fingers 802 to switch between the spread and closed positions as the coupling mechanism 606 is moved out of and into the cover 710 by the control mechanism 708 based on the dimensions of the fingers 802. Specifically, in some embodiments, the sliding pins 806 are positioned adjacent the fingers 802 in the plane of rotation such that when coupling mechanism 606 is retracted into the cover 710 the sliding pins 806 press against an upper portion of the fingers 802 causing them to rotate the fingers 802 to the closed position. Similarly, in some embodiments, when the coupling mechanism 606 is extended out of the cover 710, the sliding pins 806 press against a lower portion of the fingers 802 causing them to rotate the fingers 802 to the spread/open position. Alternatively, the lower and upper portion of the fingers 802 is able to be configured such that the retraction into the cover 710 causes the fingers 802 to switch to the spread position and the extension causes the fingers 802 to switch to the closed position. In some embodiments, the coupling mechanism 606 is configured such that the drive mechanism 808 is unable to rotate or otherwise operate unless the fingers 802 are in the closed position. Alternatively, the coupling mechanism 606 is able to comprise a drive mechanism lock (not shown) that enables the user to lock the drive mechanism 808 such that it is unable to rotate or otherwise operate until unlocked.

Figure 9:
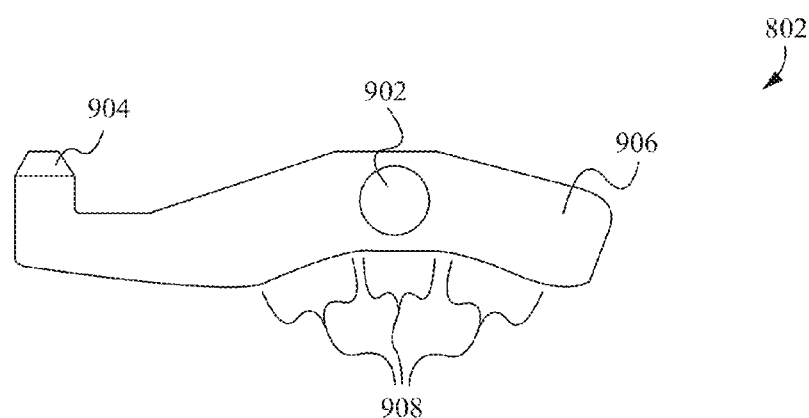
FIG. 9 illustrates a side view of a finger according to some embodiments.

FIG. 9 illustrates a side view of a finger 802 according to some embodiments. As shown in FIG. 9, the finger 802 comprises a body 906, a fingertip 904 and a finger aperture 902. In some embodiments, the finger 802 comprises one or more additional fingertips 904 and/or finger apertures 902. The finger aperture 902 is sized to receive a finger pin 804 in order to couple the finger 802 to the body 810 while enabling the finger 802 to rotate about the finger pin 804 as described above. The fingertip 904 protrudes from the body 906 such that the fingertip 904 is able to enter a gripping aperture 128. In some embodiments, the fingertip 904 comprises a beveled edge in order to facilitate the alignment and insertion of the fingertip 904 into the gripping aperture 128. As shown, the body 906 of the finger 802 comprises one or more bends 908 that (along with the walls 812) determine the extent at which the finger 802 is able to rotate about the finger pin 804. In some embodiments, each bend 908 corresponds to a desired position of the finger/fingertips 802, 904. Alternatively, the finger 802 is able to be substantially straight wherein the sliding pins 806 are able to move in order to change the angle of the fingers 802. Thus, the coupling mechanism 606 provides the advantage of enabling a user to easily control the position of the fingers 802 between an open and closed position, wherein the closed position secures the insertion instrument 602 to the bone fusion device 604 to prevent accidental slippage.

Figure 8B:
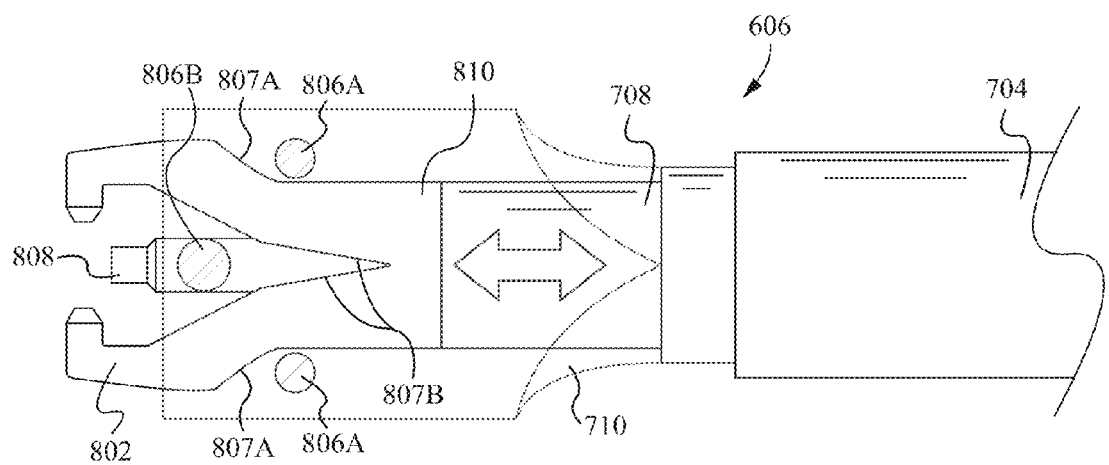
FIG. 8B illustrates a detailed top view of a different coupling mechanism within the cover according to some embodiments.

FIG. 8B illustrates a detailed top view of an alternative embodiment of the coupling mechanism 606 within the cover 710. The coupling mechanism 606 shown in FIG. 8B is able to be substantially similar to the other coupling mechanism except for the differences described herein. Specifically, as shown in FIG. 8B, the coupling mechanism 606 comprises a body 810 having one or more fingers 802 that extend from the body 810, one or more outer sliding pins 806A and one or more inner sliding pins 806B. The outer and inner sliding pins 806A, 806B are coupled to the cover 710 and cause the fingers 802 to switch between the spread and closed positions based on the dimensions of the finger walls 807A, 807B as the coupling mechanism 606 is moved out of and into the cover 710 by the control mechanism 708. In particular, as the coupling mechanism 606 is moved out of the cover 710, the inner sliding pins 806B slide between and press against the inner finger walls 807B causing the inner finger walls 807B and thus the fingers 802 to separate. Conversely, as the coupling mechanism 606 is moved into the cover 710, the outer sliding pins 806A slide onto and press against the outer finger walls 807A causing the outer finger wall 807A and thus the fingers 802 to come together or close. As a result, by selectively moving the coupling mechanism 606 with respect to the cover 710 a user is able to selectively open and close the fingers 802 as desired.

In some embodiments, the fingers 802 are able to be biased in the open position such that as they move out of the cover 710 they spread automatically and the inner sliding pins 806B are able to be omitted. Alternatively, the fingers 802 are able to be biased in the closed position such that as they move into the cover 710 they close automatically and the outer sliding pins 806A are able to be omitted. In some embodiments, the coupling mechanism 606 is configured such that the drive mechanism 808 is unable to rotate or otherwise operate unless the fingers 802 are in the closed position. Alternatively, the coupling mechanism 606 is able to comprise a drive mechanism lock (not shown) that enables the user to lock the drive mechanism 808 such that it is unable to rotate or otherwise operate until unlocked.

Figure 10:
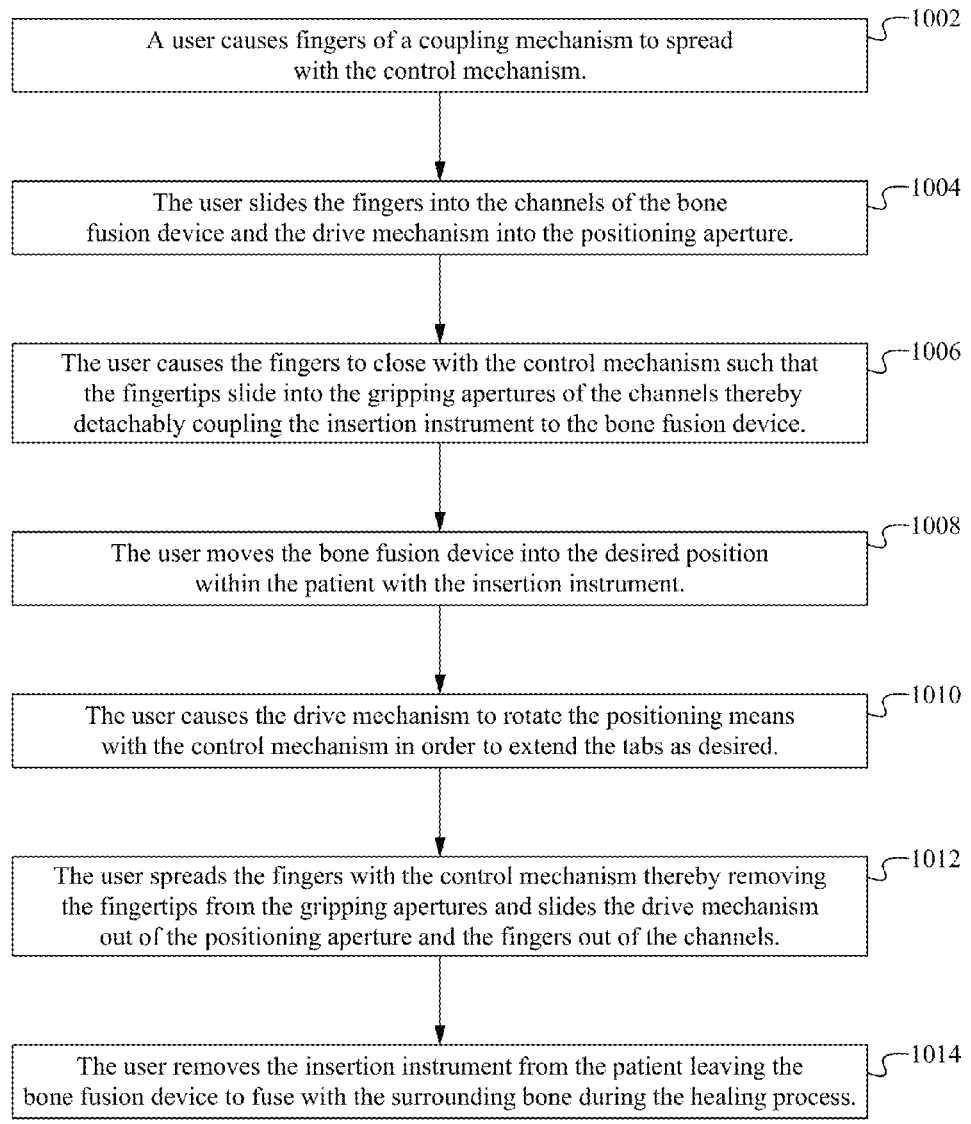
FIG. 10 illustrates a method of operating a bone fusion apparatus according to some embodiments.

A method of operation of the bone fusion apparatus 600 according to some embodiments will now be discussed in conjunction with the flow chart shown in FIG. 10. In some embodiments, one or more of the steps are able to be omitted. A user causes the fingers 802 to spread with the control mechanism 708 at the step 1002. In some embodiments, the fingers 802 are spread by pulling back on the control mechanism 708. Alternatively, the fingers 802 are able to be spread with other physical manipulations of the control mechanism 708 as are well known in the art. In some embodiments, the manner in which the control mechanism 708 causes spreading/closing of the fingers 802 is automated. Alternatively, the manner in which the control mechanism 708 causes spreading/closing of the fingers 802 is manual. The user slides the fingers 802 into the channels 122 of the bone fusion device 604 and the drive mechanism 808 into the positioning aperture 134 at the step 1004. In some embodiments, the sliding of the fingers 802 into the channels 122 and the drive mechanism 808 into the positioning aperture 134 occurs concurrently or simultaneously. The user causes the fingers 802 to close with the control mechanism 708 such that the fingertips 904 slide into the gripping apertures 128 of the channels 122 thereby detachably coupling the insertion instrument 602 to the bone fusion device 604 at the step 1006. In some embodiments, the fingers 802 are closed by pushing in on the control mechanism 708. Alternatively, the fingers 802 are able to be spread with other physical manipulations of the control mechanism 708 as are well known in the art. The user positions the bone fusion device 604 to the desired position within the patient with the insertion instrument 602 at the step 1008. In some embodiments, the desired position comprises replacing a spinal disc with the bone fusion device 604 in between two vertebrae. Alternatively, the desired position is able to comprise replacing a degenerated vertebrae with the bone fusion device 604 in between the two adjacent vertebrae and/or spinal discs. Alternatively, the insertion instrument 602 is able to be used to position other types of spinal devices such as a dynamic device, a total/partial artificial disc, a nucleus pulposus or other medical devices as are well known in the art. In some embodiments, the bone fusion device 604 is inserted anteriorly. Alternatively, the bone fusion device 604 is able to be inserted posteriorly, laterally or transforaminaly.

The user causes the drive mechanism 808 to rotate the positioning means 108 with the control mechanism 708 in order to extend the plates 130 as desired at the step 1010. In some embodiments, the user rotates the drive mechanism 808 in order to rotate the positioning means 108. Alternatively, the user is able to otherwise manipulate the control mechanism 708 in order to rotate the drive mechanism 808. In some embodiments, the manner in which the control mechanism 708 causes the rotation of the drive mechanism 808 is automated. Alternatively, the manner in which the control mechanism 708 causes the rotation of the drive mechanism 808 is manual. In some embodiments, the readout 706 displays and dynamically adjusts a measurement of the amount of the current expansion of the plates 130 outside of the frame 114 as the control mechanism 708 rotates the drive mechanism 808. In some embodiments, the readout or indicator 706 comprises an adjustable and/or removable scale. In some embodiments, the scale is able to be attached and/or adjusted based on the bone fusion device 604 such that the readout 706 outputs accurate readings of the expansion amount of the plates 130. In some embodiments, the measurement of the amount of current expansion of the plates 130 outside of the frame 114 comprises the amount of rotations of the drive mechanism 808 in one or more directions since the drive mechanism 808 was inserted into the positioning aperture. The user spreads the fingers 802 with the control mechanism 708 thereby removing the fingertips 904 from the gripping apertures 128 and slides the drive mechanism 808 out of the positioning aperture 134 and the fingers 802 out of the channels 122 at the step 1012. The user then removes the insertion instrument 602 from the patient leaving the bone fusion device 604 to fuse with the surrounding bone during the healing process at the step 1014. As a result, the method of operating the bone fusion apparatus 600 enables the surgeon to securely position the bone fusion device 604 and extend the plates 130 as needed with minimal possibility of the drive mechanism 808 slipping out of the positioning aperture 134. Specifically, by coupling the fingertips 904 within the gripping apertures 128 and the fingers 802 within the channels 122, the insertion instrument 602 is prevented from being pulled, pushed or twisted away from the bone fusion device 604. Thus, the procedure is made both safer and more efficient.

Figure 11:
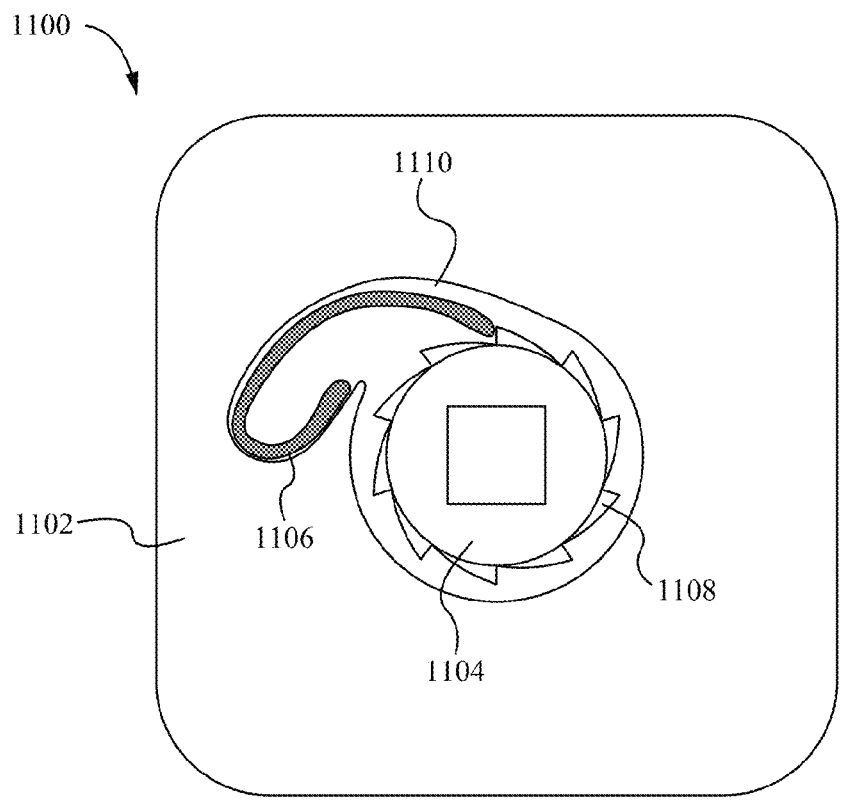
FIG. 11 illustrates a bone fusion device having a rachet mechanism according to some embodiments.

FIG. 11 illustrates a bone fusion device 1100 having a rachet mechanism according to some embodiments. The bone fusion device 1100 shown in FIG. 11 is able to be substantially similar to the other bone fusion devices except for the differences described herein. In particular, the bone fusion device 1100 comprises a body 1102, a positioning means 1104 and a rachet mechanism including a pawl 1106 and one or more gear teeth 1108 on the perimeter of the positioning means 1104. As shown in FIG. 11, the pawl 1106 is positioned within a cavity 1110 of the body 1102 that is adjacent to the positioning means 1104 such that the arm of the pawl 1106 is able to abut or be in communication with the one or more gear teeth 1108. As a result, the pawl 1106 is able to permit the positioning means 1104 to rotate in one direction while preventing the positioning means 1104 from rotating back in the opposite direction. Specifically, the size and/or angles of the gear teeth 1108 are able to be adjusted such that as the positioning means 1104 rotate in a first direction the pawl 1106 is able to slide over the gear teeth 1108 due to the angle of the pawl 1106 and/or the angle of a first side of the gear teeth 1108. Contrarily, if the positioning means 1104 starts to rotate in a second or opposite direction the pawl 1106 is unable to slide over the gear teeth 1108 due to the angle of the pawl 1106 and/or the angle of a second or opposite side of the gear teeth 1108 thereby stopping or preventing the rotation of the positioning means in the second or opposite direction. As a result, the bone fusion device 1100 having a rachet mechanism provides the benefit of ensuring that the tabs stay in place when extended because the rachet mechanism prevents them from retracting.

In some embodiments, the rachet mechanism comprises a release mechanism (not shown) that when activated separates or changes the dynamic of the pawl 1106 and the gear teeth 1108 such that the positioning means 1104 is able to rotate in the second or opposite direction without being stopped by the pawl 1106. Alternatively, the angle of the pawl 1106 and/or gear teeth 1108 of the rachet mechanism are able to be configured such that with a desired force F the positioning means 1104 is able to be rotated in the second or opposite direction despite the presence of the pawl 1106. In particular, the desired force F is able to be greater than the maximum force that would occur on the tabs within a patient after implantation such that the rotation in the second direction would only occur if the surgeon needed to rotate the positioning means 1104 in that direction. In some embodiments, the pawl 1106 comprises nitinol or stainless steel. Alternatively, the pawl 1106 is able to comprise other types of suitable materials as are well known in the art. In some embodiments, the first direction of rotation corresponds to the direction required to extend the tabs of the device 1100 and the second direction corresponds to the direction required to retract the tabs of the device. Alternatively, the first direction is able to correspond to the direction required to retract the tabs of the device 1100 and the second direction corresponds to the direction required to extend the tabs of the device.

Figure 12A:
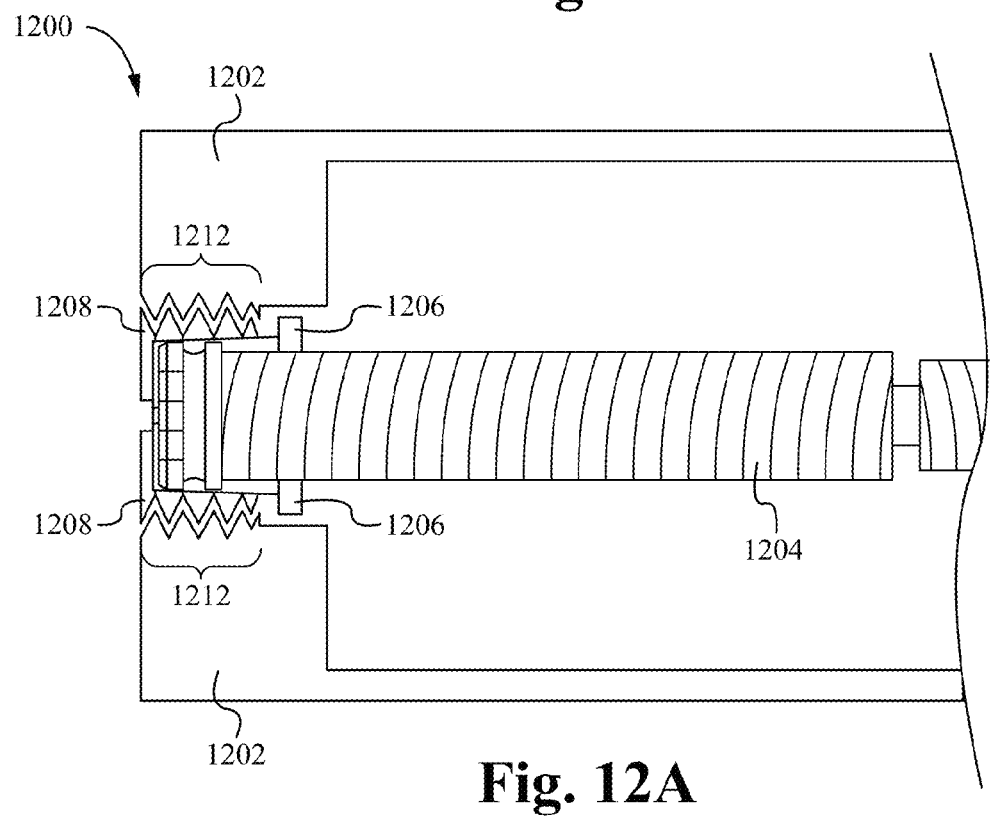
FIG. 12A illustrates a cross sectional view of a bone fusion device having a lock mechanism according to some embodiments.
Figure 12B:
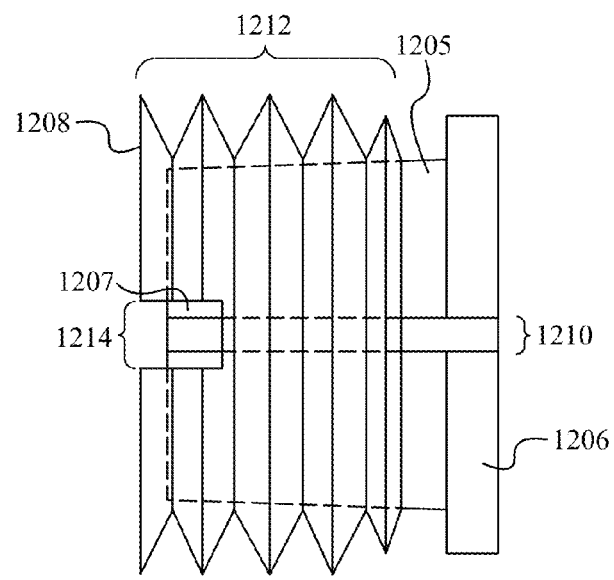
FIG. 12B illustrates a side view of a lock mechanism according to some embodiments

FIG. 12A illustrates a cross sectional view of a bone fusion device 1200 having a lock mechanism according to some embodiments. The bone fusion device 1200 shown in FIG. 12A is able to be substantially similar to the other bone fusion devices except for the differences described herein. In particular, the bone fusion device 1200 comprises a body 1202, a positioning means 1204 and a lock mechanism including a collar 1206 and a choke 1208. As shown in FIG. 12B, the collar 1206 has a thick end 1205, a narrow end 1207 and a gap 1210 and the choke 1208 is configured to fit around the narrow end 1207 of the collar 1206. As a result, if the choke 1208 is pushed or otherwise forced down on the collar 1206 towards the thick end 1205, it causes the gap 1210 of the collar 1206 to contract thereby continually reducing the circumference of the collar 1206 as it moves until the gap 1210 is gone. Similarly, if the choke 1208 is moved back toward the narrow end 1207 of the collar 1206, the gap 1210 is able to continually increase up to its original size increasing the circumference of the collar 1206 as permitted by the inner circumference of the choke 1208. As shown in FIG. 12A, the lock mechanism 1206, 1208 is positioned around the end of the positioning means 1204 within an aperture at an end of the body 1202. As a result, when the choke 1208 causes the circumference of the collar 1206 to reduce, it causes the collar 1206 to provide a choking force on the positioning means 1204 such that the positioning means 1204 are unable to rotate due to the friction between the collar 1206 and the surface of the positioning means 1204. As a result, the lock mechanism is able to provide the benefit of enabling the positioning means and thus the tabs to be locked in place thereby reducing the risk of the tabs undesirably retracting.

In some embodiments, the choke 1208 has threading 1212 that corresponds to threading of the body 1202 such that if the choke 1208 is rotated the threading 1212 causes the choke 1208 to move further in or out of the aperture of the body 1202 and thereby move with respect to the collar 1206 in order to lock or unlock the positioning means 1204 as described above. In such embodiments, the choke 1208 is able to have one or more cutouts 1214 for receiving a tool for rotating the choke 1208. Alternatively, the threading 1212 is able to act as "snap-fit" stops or ridges/valleys that correspond to ridges/valleys of the body 1202 such that if the choke 1208 is pushed further into the aperture of the body 1202 and toward the thick end 1205 of the collar 1206, the ridges of the threading 1212 compress and then spring/snap into the valleys of the body 1202 thereby preventing the choke 1208 from being forced back away from end thick end 1205 of the collar 1206. In some embodiments, the thickness of the collar 1206 gradually changes from the narrow end 1207 to the thick end 1205. Alternatively, the thickness of the collar 1206 is able to change in one or more increments. For example, the thickness is able to remain substantially constant until the next increment is reached.

Figure 13A:
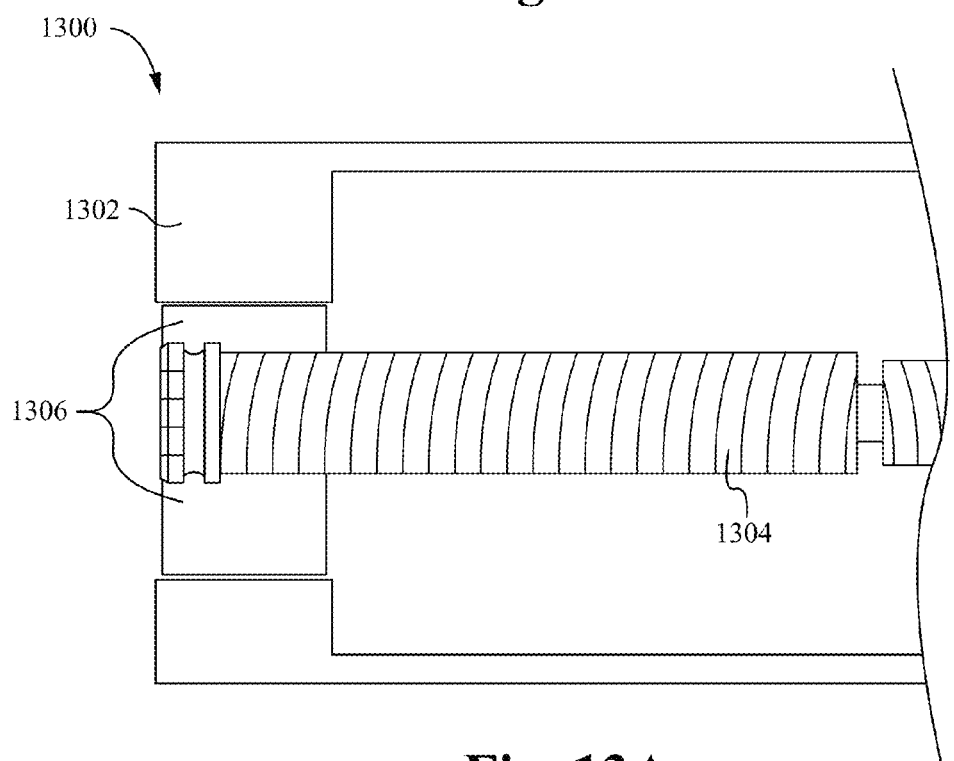
FIG. 13A illustrates a side cross sectional view of a bone fusion device having an oblong locking mechanism according to some embodiments.
Figure 13B:
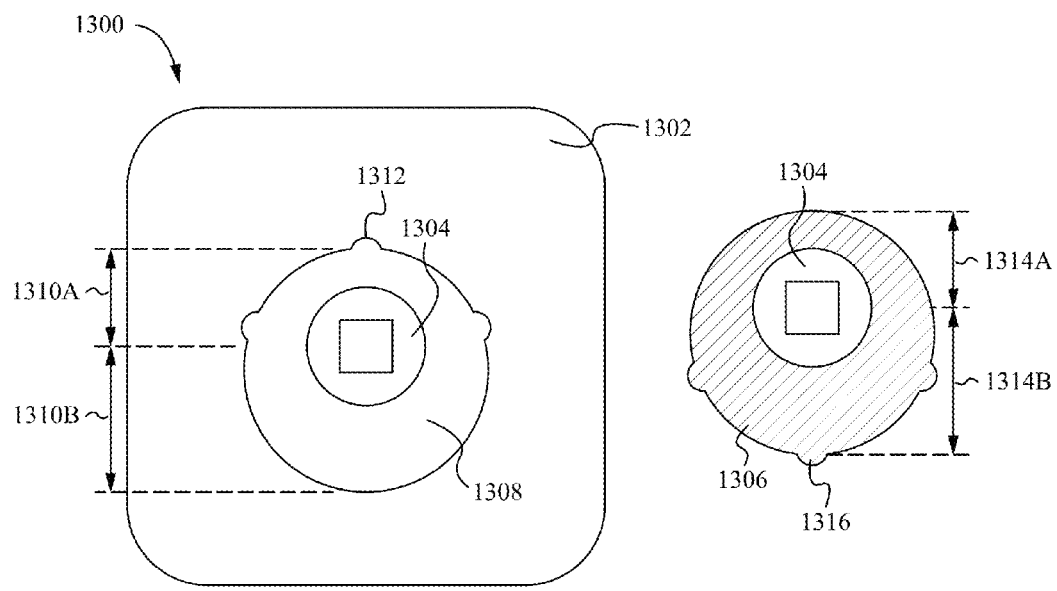
FIG. 13B illustrates a frontal view of a body of the bone fusion device and the oblong locking mechanism according to some embodiments.

FIGS. 13A-F illustrate a bone fusion device 1300 having an oblong lock mechanism according to some embodiments. The bone fusion device 1300 shown in FIGS. 13A-F is able to be substantially similar to the other bone fusion devices except for the differences described herein. As shown in FIGS. 13A and 13B, which illustrate side cross sectional and frontal views respectively, the bone fusion device 1300 comprises a body 1302, positioning means 1304 within the body 1203 and an oblong locking member 1306 surrounding one end of the positioning means 1304 and having one or more bumps 1316. The body 1302 comprises an aperture 1308 for receiving the positioning means 1304 and the locking member 1306, wherein the aperture 1308 includes one or more notches 1312 that are able to selectively receive the one or more bumps 1316. In particular, as shown in FIG. 13B, the aperture 1308 is oblong such that it has a short side 1310A and a long side 1310B that correspond to a short side 1314A and long side 1314B of the oblong locking member 1306.

Figure 13C:
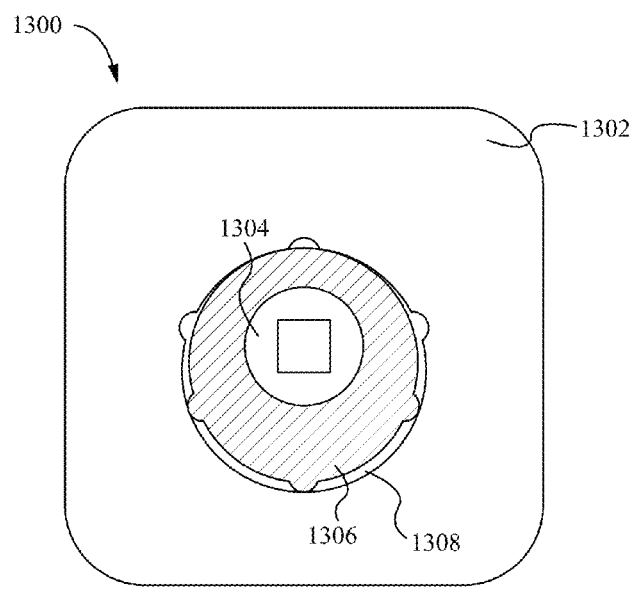
FIG. 13C illustrates a frontal view of a bone fusion device having an oblong locking mechanism in the unlocked position according to some embodiments.
Figure 13D:
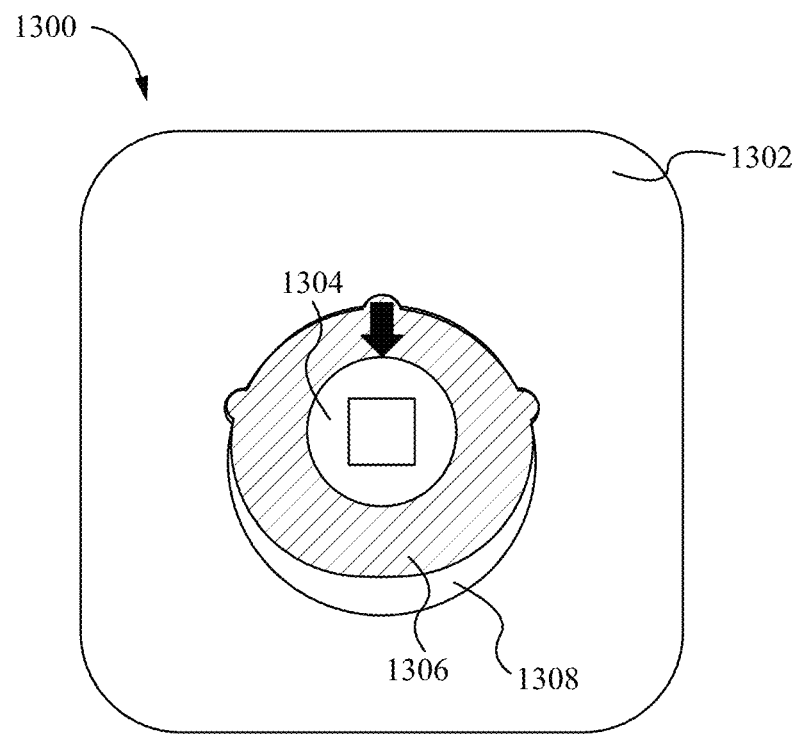
FIG. 13D illustrates a frontal view of a bone fusion device having an oblong locking mechanism in the locked position according to some embodiments.

As a result, as shown in FIG. 13D, the oblong locking member 1306 is able to be rotated into a "locked" position where the short side 1314A of the locking member 1306 is positioned within the long side 1310B of the aperture 1308 and the long side 1314B of the locking member 1306 is positioned within the short side 1310A of the aperture 1308. In this locked position, the positioning means 1304 will be unable to rotate freely as pressure is applied to the positioning means 1304 by the long side 1314B of the locking member 1306 in the direction indicated by the arrow because the long side 1314B is under compression by the short side 1310A of the aperture 1308. In particular, the force applied to the positioning means 1304 by the locking member 1306 in the locked position increases the friction between the positioning means 1304 and the locking member 1306 such that the positioning means 1304 is unable to rotate. In contrast, as shown in FIG. 13C, the oblong locking member 1306 is able to be rotated into an "unlocked" position where the short side 1314A of the locking member 1306 is positioned within the short side 1310A of the aperture 1308 and the long side 1314B of the locking member 1306 is positioned within the long side 1310B of the aperture 1308. In this "unlocked" position, the positioning means 1304 will be able to rotate freely as little or no pressure is applied to the positioning means 1304 by the locking member 1306 because the locking member 1306 is not under compression by the aperture 1308. As a result, the lock mechanism is able to provide the benefit of enabling the positioning means and thus the tabs to be locked in place thereby reducing the risk of the tabs undesirably retracting.

In some embodiments, the oblong locking member 1306 comprises PEEK. Alternatively, the oblong locking member 1306 is able to comprise other types of biocompatable materials that are flexible such that they are able to be compressed and apply a stopping force to the positioning means 1304. In some embodiments, the notches 1312 and the bumps 1316 are configured such that one or more of the bumps 1316 slide into the notches 1312 when the oblong locking member 1306 is in either the locked or unlocked positions. In particular, in such embodiments the bumps 1316 and notches 1312 are able to provide an indication that the locking member 1306 has been fully rotated in the locked or unlocked position as well as preventing the oblong locking member 1306 from slipping out of the locked or unlocked position. In some embodiments, the oblong locking member 1306 comprising one or more apertures that facilitate the rotation of the locking member 1306 by a tool or user.

Figure 13E:
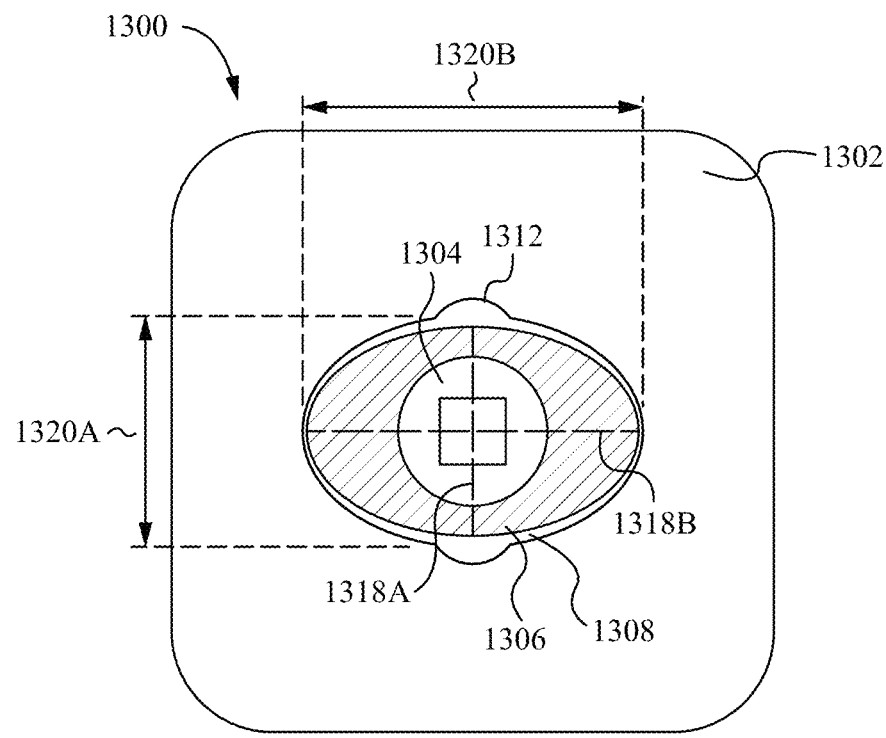
FIG. 13E illustrates a frontal view of a bone fusion device having an oblong locking mechanism in the unlocked position according to some embodiments.
Figure 13F:
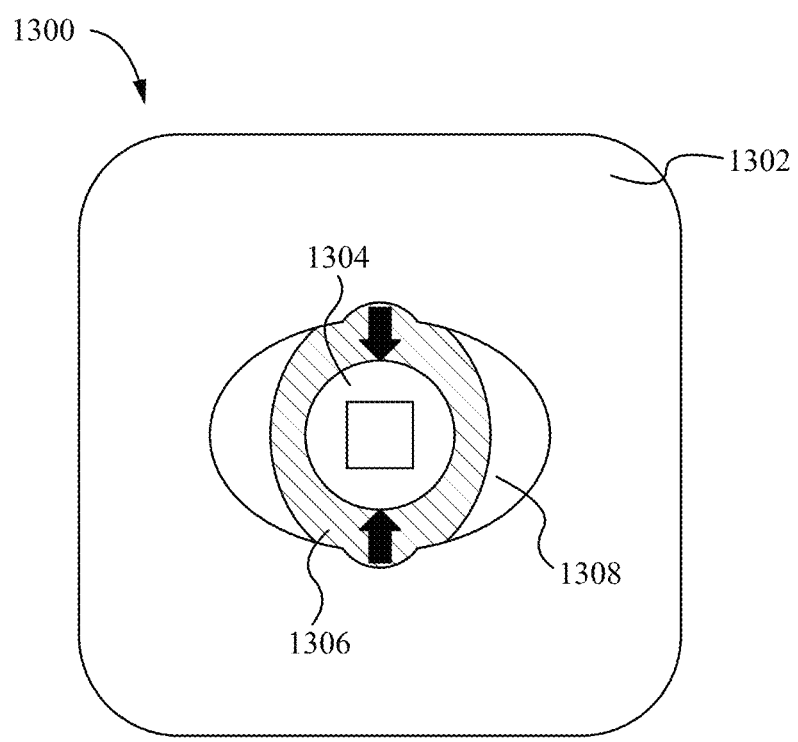
FIG. 13F illustrates a frontal view of a bone fusion device having an oblong locking mechanism in the locked position according to some embodiments.

FIGS. 13E and 13F illustrate an alternate embodiment of the bone fusion device 1300 having the oblong locking mechanism according to some embodiments. In particular, as shown in FIGS. 13E and 13F, the aperture 1308 and the oblong locking member 1306 are ovular such that they each have a short dimension 1318A, 1320A and a long dimension 1318B, 1320B. As a result, when rotated into a "locked" position as shown in FIG. 13F, the positioning means 1304 is unable to rotate freely as pressure is applied to the positioning means 1304 from both sides along the long dimension 1318B of the locking member 1306 in the direction indicated by the arrows because the long dimension 1318B is under compression by the short dimension 1320A of the aperture 1308. In contrast, as shown in FIG. 13E, the oblong locking member 1306 is able to be rotated into an "unlocked" position where the short dimension 1318A of the locking member 1306 is positioned within the short dimension 1320A of the aperture 1308 and the long dimension 1318B of the locking member 1306 is positioned within the long dimension 1320B of the aperture 1308. Like in FIG. 13C, in this "unlocked" position the positioning means 1304 will be able to rotate freely as little or no pressure is applied to the positioning means 1304 by the locking member 1306 because the locking member 1306 is not under compression by the aperture 1308. In some embodiments, the aperture 1308 comprises one or more notches 1312 that are configured such that ends of the long dimension 1318B slide into the notches 1312 when the oblong locking member 1306 is in the locked positions. In particular, in such embodiments the notches 1312 are able to provide an indication that the locking member 1306 has been fully rotated in the locked or unlocked position as well as preventing the oblong locking member 1306 from slipping out of the locked or unlocked position. Alternatively, the oblong locking member 1306 is able to comprise on or more bumps 1316 for sliding into the notches 1312 in addition to or in lieu of the ends of the long dimension 1318B. As a result, the lock mechanism is able to provide the benefit of enabling the positioning means and thus the tabs to be locked in place thereby reducing the risk of the tabs undesirably retracting.

The embodiments of the lock mechanism described herein and illustrated in FIGS. 11-13 are examples of particular lock mechanisms. As will be apparent to those skilled in the art, other appropriate lock mechanisms are able to be utilized within the bone fusion device described herein, to keep the rotatable fastener from moving.

Thus, the bone fusion device, apparatus and method described herein has numerous advantages. Specifically, the fingers and fingertips coupled to the channels having gripping apertures ensure the non-slippage of the driving mechanism during the operation of the bone fusion apparatus. Further, the lock mechanism is able to provide the benefit of enabling the positioning means and thus the tabs to be locked in place thereby reducing the risk of the tabs undesirably retracting. Moreover, the small size of the single plate embodiments enables the use of smaller incisions and a more compact design. Also, as mentioned above, the method of use requires only a small incision and minimally invasive surgical procedure advantageously promoting health and rapid recovery by the patient. Indeed, bone growth occurs around the bone fusion device and particularly at the locations of the extended plates, such that the bone fusion device is further secured by the bone growth, which further promotes a superior, robust bone fusion result.

The present invention has been described in terms of specific embodiments incorporating details to facilitate the understanding of principles of construction and operation of the invention. Such reference herein to specific embodiments and details thereof is not intended to limit the scope of the claims appended hereto. It will be apparent to those skilled in the art that modification may be made in the embodiments chosen for illustration without departing from the spirit and scope of the invention. For example, it should be noted that although the above bone fusion devices are described in reference to a pair of extending blocks, a pair of screws, and wherein each plate is shaped such that the ends are larger than the middle, and the size of the plate gradually increases while going from the middle to the ends, the use of a single extending block in the above embodiments is contemplated. Specifically, if using a single extending block, the above embodiments would operate the same except the positioning means would comprise a single screw that when engaged would cause the single extending block to move from one end of the screw to the other end thereby exerting a force against the plates such that they move into the extended position. In such embodiments, each plate is shaped such that one end is larger than the opposite end, and the size of the plate gradually increases going from the smaller end to the larger end.

What is claimed is:

1. A bone fusion system for inserting a bone fusion device into a desired location, the system comprising:
   a. an insertion instrument comprising an elongated body having a central axis and a coupling mechanism partially housed by the elongated body and having a control mechanism and a plurality of fingers configured to move between a closed position wherein the fingers are close together to a spread position wherein the fingers are farther apart based on manipulation of the control mechanism and further wherein one or more of the fingers comprise a fingertip that protrudes laterally from the finger; and
   b. a bone fusion device having a fusion body, a first extendable tab and a second extendable tab, wherein the fusion body of the bone fusion device comprises a front end, an interior cavity and one or more surface channels having sufficient size to receive the fingers within the channels and positioned along an exterior surface of the fusion body and further wherein the channels are accessible from the front end and extend through a plane perpendicular to the front end, and is detachably coupled to the insertion instrument by the coupling mechanism, wherein the channels are dimensioned and located on the fusion body such that when the fingers are within the channels the central axis of the elongated body is perpendicular to a smallest profile of the bone fusion device, and further wherein each of the surface channels comprise a gripping aperture positioned within the surface channels for receiving the fingertip of the fingers.

2. The system of claim 1, wherein the bone fusion device further comprises a positioning element having a positioning aperture and positioned through the front end and within the interior cavity of the fusion body, and further wherein the positioning element is mechanically coupled with the first and second extendable tabs such that moving the positioning element causes the first and second extendable tabs to move with respect to the fusion body.

3. The system of claim 2, wherein the surface channels are positioned along the exterior surface on a plane perpendicular to the positioning aperture of the positioning element such that the fingers of the gripping apparatus are able to enter the one or more surface channels by moving parallel to the plane.

4. The system of claim 3, wherein the insertion instrument further comprises a drive mechanism configured to engage with and selectively rotate the positioning aperture when the insertion instrument is coupled to the bone fusion device.

5. The system of claim 4, wherein the control mechanism is coupled with the drive mechanism such that the drive mechanism is able to be rotated by manipulating the control mechanism.

6. The system of claim 5, wherein the insertion instrument is configured to prevent rotation of the drive mechanism if the fingers are not in the closed position.

7. The system of claim 6, wherein the insertion instrument comprises a locking mechanism that when activated by a trigger prevents rotation of the drive mechanism until the locking mechanism is deactivated by the trigger.

8. The system of claim 7, wherein the insertion instrument comprises an indicator that indicates data corresponding to the amount of rotation of the drive mechanism.

9. The system of claim 8, wherein the data indicated by the indicator indicates the current position of the tabs relative to the fusion body of the bone fusion device.

10. The system of claim 9, wherein the indicator is adjustable such that the indicator will indicate different data corresponding to the same amount of rotation of the drive mechanism based on the bone fusion device currently coupled to the insertion instrument.

11. A bone fusion system for inserting a bone fusion device into a desired location, the system comprising:
   a. an insertion instrument comprising a coupling mechanism having a control mechanism and a plurality of fingers configured to move between a closed position wherein the fingers are close together to a spread position wherein the fingers are farther apart based on manipulation of the control mechanism and further wherein one or more of the fingers comprise a fingertip that protrudes laterally from the finger; and
   b. a bone fusion device having a body and a plurality of extendable tabs movably coupled to the body such that the entirety of each of the extendable tabs is able to move with respect to the body, the plurality of extendable tabs positioned parallel to each other, wherein the body of the bone fusion device comprises a front end, an interior cavity and one or more surface channels having sufficient size to receive the fingers within the channels and positioned along an exterior surface of the body of the bone fusion device and further wherein the channels are accessible from the front end and extend through a plane perpendicular to the front end, and is detachably coupled to the insertion instrument by the coupling mechanism, wherein the surface channels are positioned along the exterior surface on a plane perpendicular to a positioning aperture of a positioning element such that the fingers of the gripping apparatus are able to enter the one or more surface channels by moving parallel to the plane and further wherein each of the surface channels comprise a gripping aperture for receiving the fingertip of the fingers of the gripping apparatus positioned within the surface channels.

12. The system of claim 11, wherein the insertion instrument further comprises a drive mechanism configured to engage with and selectively rotate the positioning aperture when the insertion instrument is coupled to the bone fusion device.

13. A bone fusion system for inserting a bone fusion device into a desired location, the system comprising:
   a. an insertion instrument comprising an elongated body and a coupling mechanism partially housed by the elongated body and having a control mechanism and a plurality of fingers configured to move between a closed position wherein the fingers are close together to a spread position wherein the fingers are farther apart based on manipulation of the control mechanism, wherein the insertion instrument further comprises a drive mechanism configured to engage with and selectively rotate the positioning aperture when the insertion instrument is coupled to the bone fusion device, and further wherein the control mechanism is coupled with the drive mechanism such that the drive mechanism is able to be rotated by manipulating the control mechanism, wherein the insertion instrument prevents rotation of the drive mechanism if the fingers are not in the closed position and further wherein the insertion instrument comprises a locking mechanism that when activated by a trigger prevents rotation of the drive mechanism until the locking mechanism is deactivated by the trigger; and
   b. a bone fusion device having a fusion body and a plurality of extendable tabs movably coupled to the fusion body such that the entirety of each of the extendable tabs is able to move with respect to the fusion body, the plurality of extendable tabs positioned parallel to each other, wherein the fusion body of the bone fusion device comprises one or more surface channels having sufficient size to receive the fingers within the channels and positioned along an exterior surface of the fusion body, and is detachably coupled to the insertion instrument by the coupling mechanism, wherein the surface channels are positioned along the exterior surface on a plane perpendicular to a positioning aperture of a positioning element such that the fingers of the gripping apparatus are able to enter the one or more surface channels by moving parallel to the plane.

14. The system of claim 13, wherein the insertion instrument comprises an indicator that indicates data corresponding to the amount of rotation of the drive mechanism.

15. The system of claim 14, wherein the data indicated by the indicator indicates the current position of the tabs relative to the fusion body of the bone fusion device.

16. The system of claim 15, wherein the indicator is adjustable such that the indicator will indicate different data corresponding to the same amount of rotation of the drive mechanism based on the bone fusion device currently coupled to the insertion instrument.

17. A bone fusion system for inserting a bone fusion device into a desired location, the system comprising:
   a. an insertion instrument comprising an elongated body having a central axis and a coupling mechanism partially housed by the elongated body and having a control mechanism and a plurality of fingers configured to move between a closed position wherein the fingers are close together to a spread position wherein the fingers are farther apart based on manipulation of the control mechanism; and
   b. a bone fusion device having a fusion body and one or more extendable tabs, wherein the fusion body of the bone fusion device comprises a first surface channel positioned on a first side of the bone fusion device above a horizontal midline of the bone fusion device between the extendable tabs and a second surface channel positioned on a second side of the bone fusion device below the horizontal midline, the first and second surface channels having sufficient size to receive the fingers within the channels and detachably coupled to the insertion instrument by the coupling mechanism.

* * * * *